United States Patent
Kim

(10) Patent No.: US 6,232,461 B1
(45) Date of Patent: May 15, 2001

(54) NUCLEIC ACID MOLECULE ENCODING ABSCISIC ACID RESPONSIVE ELEMENT-BINDING RACTOR 4

(75) Inventor: Soo Young Kim, Kwangju (KR)

(73) Assignee: Korea Kumho Petrochemical Company, Ltd., Seoul (KR)

( * ) Notice: Subject to any disclaimer, the term of this patent is extended or adjusted under 35 U.S.C. 154(b) by 0 days.

(21) Appl. No.: 09/665,309

(22) Filed: Sep. 19, 2000

Related U.S. Application Data

(62) Division of application No. 09/416,050, filed on Oct. 12, 1999.

(51) Int. Cl.[7] .................................................. C12N 15/29
(52) U.S. Cl. ............................................................. 536/23.6
(58) Field of Search ............................................. 536/23.6

(56) References Cited

PUBLICATIONS

Leung & Giraudat, Abscisic Acid Signal Transduction, Annu. Rev. Plant Physiol. Plant Mol. Bio., 1998, 49:199–222.

Kim et al., Isolation of a novel class of bZIP transcription factors that interact with ABA–responsive and embryo–specification elements in the Dc3 promoter using a modified yeast one–hybrid system, The Plant Journal, 1997, 11(6):1237–1251.

Nakagawa et al., A rice bZIP protein, designated OSBZ8, is rapidly induced by abscisic acid, The Plant Journal, 1996, 9(2):217–227.

Lu et al., Transcription Factor Veracity: Is GBF3 Responsible for ABA–Regulated Expression of Arabidopsis Adh?, The Plant Cell., 1996, 8:847–857.

Oeda et al., A tobacco bZIP transcription activator (TAF–1) bind to a G–box–like motif conserved in plant genes, The EMBO Journal, 1991, 10(7):1793–1802.

Guiltinan et al., A Plant Leucine Zipper Protein That Recognizes an Abscisic Acid Responsive Element, 1990, Science, 250:267–271.

*Primary Examiner*—Terry McKelvey
(74) *Attorney, Agent, or Firm*—Kenyon & Kenyon

(57) ABSTRACT

A nucleic acid molecule encoding the Abscisic acid responsive element binding factor 4 (ABF4) was isolated and its nucleotide sequence determined. ABF4 belongs to the ABF family of factors which bind abscisic acid responsive elements in plants. Expression of ABFs is inducible by abscisic acid and various stress treatments. ABFs have the potential to activate a large number of abscisic acid/stress responsive genes and thus a nucleic acid molecule encoding ABF4 can be used to generate transgenic plants that are tolerant to multiple environmental stresses.

3 Claims, 15 Drawing Sheets

```
AAAGGGTCTGATTCGTTTGTTTTTTCACTGAAGAATTTGGAAGGAAGTGATTCCGTTGTG    60
AAACAGAAAAGAAGTATGGGTACTCACATTGATATCAACAACTTAGGCGGCGATACTTCT   120
                M  G  T  H  I  D  I  N  N  L  G  G  D  T  S
AGAGGGAATGAGTCAAAGCCATTGGCGAGGCAGTCTTCGTTATATTCCTTAACGTTTGAT   180
 R  G  N  E  S  K  P  L  A  R  Q  S  S  L  Y  S  L  T  F  D
GAGCTTCAGAGCACATTAGGTGAGCCGGGGAAAGATTTTGGGTCTATGAATATGGATGAG   240
 E  L  Q  S  T  L  G  E  P  G  K  D  F  G  S  M  N  M  D  E
TTACTCAAGAACATATGGACTGCTGAGGATACTCAAGCCTTTATGACTACTACATCTTCG   300
 L  L  K  N  I  W  T  A  E  D  T  Q  A  F  M  T  T  T  S  S
GTTGCAGCCCCGGGACCTAGTGGTTTTGTTCCGGGAGGAAATGGTTTACAGAGGCAAGGC   360
 V  A  A  P  G  P  S  G  F  V  P  G  G  N  G  L  Q  R  Q  G
TCCTTGACCTTGCCTAGAACGCTTAGTCAGAAGACTGTCGATGAAGTCTGGAAATACCTG   420
 S  L  T  L  P  R  T  L  S  Q  K  T  V  D  E  V  W  K  Y  L
AATTCGAAAGAAGGTAGTAATGGGAATACTGGAACGGATGCGCTTGAGAGGCAACAGACT   480
 N  S  K  E  G  S  N  G  N  T  G  T  D  A  L  E  R  Q  Q  T
TTAGGGGAAATGACTCTGGAAGATTTCTTACTCCGTGCTGGCGTTGTTAAAGAAGATAAT   540
 L  G  E  M  T  L  E  D  F  L  L  R  A  G  V  V  K  E  D  N
ACTCAGCAGAACGAAAACAGTAGTAGCGGGTTTTATGCTAACAACGGTGCTGCTGGTTTG   600
 T  Q  Q  N  E  N  S  S  S  G  F  Y  A  N  N  G  A  A  G  L
GAGTTTGGATTTGGTCAGCCGAATCAAAACAGCATATCGTTCAACGGGAACAATAGTTCT   660
 E  F  G  F  G  Q  P  N  Q  N  S  I  S  F  N  G  N  N  S  S
ATGATCATGAATCAAGCACCTGGTTTAGGCCTCAAAGTTGGTGGAACCATGCAGCAGCAG   720
 M  I  M  N  Q  A  P  G  L  G  L  K  V  G  G  T  M  Q  Q  Q
CAGCAGCCACATCAGCAGCAGTTGCAGCAGCCACATCAGAGACTGCCTCCAACTATCTTT   780
 Q  Q  P  H  Q  Q  Q  L  Q  Q  P  H  Q  R  L  P  P  T  I  F
CCAAAACAAGCGAATGTAACATTTGCGGCGCCTGTAAATATGGTCAACAGGGGTTTATTT   840
 P  K  Q  A  N  V  T  F  A  A  P  V  N  M  V  N  R  G  L  F
GAGACTAGCGCAGATGGTCCAGCCAACAGTAATATGGGAGGAGCAGGGGGTACTGTTACA   900
 E  T  S  A  D  G  P  A  N  S  N  M  G  G  A  G  G  T  V  T
GCTACTTCTCCTGGGACGAGCAGTGCAGAAAACAATACTTGGTCATCACCAGTTCCTTAC   960
 A  T  S  P  G  T  S  S  A  E  N  N  T  W  S  S  P  V  P  Y
GTGTTTGGTCGGGGAAGAAGAAGCAATACGGGCCTGGAGAAGGTTGTTGAGAGAAGGCAA  1020
 V  F  G  R  G  R  R  S  N  T  G  L  E  K  V  V  E  R  R  Q
AAGAGAATGATCAAGAATCGGGAATCCGCTGCTAGATCAAGGGCTCGAAAACAGGCTTAT  1080
 K  R  M  I  K  N  R  E  S  A  A  R  S  R  A  R  K  Q  A  Y
ACCTTGGAACTGGAAGCTGAGATTGAAAGTCTCAAGCTAGTGAATCAAGATTTGCAGAAG  1140
 T  L  E  L  E  A  E  I  E  S  L  K  L  V  N  Q  D  L  Q  K
AAACAGGCTGAAATAATGAAAACCCATAATAGTGAGCTAAAGGAATTTTCGAAGCAGCCT  1200
 K  Q  A  E  I  M  K  T  H  N  S  E  L  K  E  F  S  K  Q  P
CCATTGCTGGCCAAAAGACAATGCTTGAGAAGAACCCTTACCGGTCCGTGGTAAGAAGGT  1260
 P  L  L  A  K  R  Q  C  L  R  R  T  L  T  G  P  W
GAAGTCAAAGCAAGAAGAACCTGCTAATGTAATACAGGACCACTCAAAAGGAAGACACTG  1320
GGAGAGTAATATGTAATAGAAGATAGTGCTACTGTACAGGAGAAATTACAGAGACGCTTA  1380
CAATGTAGAAATCTTTTGAGCTGAATTTAACTAAGAGTGCAGTCTGTGTAGAGTATGAGA  1440
GCTTTCAATATGAATTCATAATTTTCATAAACATATGTAAAACTTTCAGATTTAGCTATA  1500
GAGAAGATGTGACTAAAAAAAAAAAAAAAAAAAAAAAAAAAAAAAAAAAAAAAAAAAAAA  1560
AAAAAAAAAAAAAAAAAA                                           1578
```

FIG.2A

```
CCCAAACGAAGAACCAAACATTTTGAAATTTTTTGGGAAAATTACAAAGCACACGAATTT         60
AGCAAAAAGATCCAGTTATTAGGTGGAAGCAGATTTTGTAGAAAAATGGATGGTAGTATG        120
                                                 M  D  G  S  M
AATTTGGGGAATGAGCCACCAGGAGATGGTGGTGGAGGTGGAGGGTTGACTAGACAAGGT        180
 N  L  G  N  E  P  P  G  D  G  G  G  G  G  L  T  R  Q  G
TCGATATACTCGTTGACGTTTGATGAGTTTCAGAGCAGTGTAGGGAAAGATTTTGGGTCA        240
 S  I  Y  S  L  T  F  D  E  F  Q  S  S  V  G  K  D  F  G  S
ATGAACATGGATGAGTTGTTAAAGAATATATGGAGTGCTGAAGAAACACAAGCCATGGCT        300
 M  N  M  D  E  L  L  K  N  I  W  S  A  E  E  T  Q  A  M  A
AGTGGTGTGGTTCCAGTTCTTGGTGGAGGTCAAGAGGGTTTGCAGCTGCAGAGGCAAGGC        360
 S  G  V  V  P  V  L  G  G  G  Q  E  G  L  Q  L  Q  R  Q  G
TCGTTGACTCTGCCTCGAACGCTTAGTCAGAAGACGGTTGATCAAGTTTGGAAAGATCTA        420
 S  L  T  L  P  R  T  L  S  Q  K  T  V  D  Q  V  W  K  D  L
TCCAAAGTTGGAAGTAGTGGAGTAGGGGGAAGTAACTTGTCTCAGGTGGCTCAGGCTCAG        480
 S  K  V  G  S  S  G  V  G  G  S  N  L  S  Q  V  A  Q  A  Q
AGTCAGAGTCAGAGTCAGAGGCAGCAAACATTAGGTGAAGTAACTTTGGAGGAGTTTTTG        540
 S  Q  S  Q  S  Q  R  Q  Q  T  L  G  E  V  T  L  E  E  F  L
GTTCGTGCTGGTGTTGTGAGAGAGGAAGCTCAGGTTGCTGCAAGAGCTCAGATTGCTGAG        600
 V  R  A  G  V  V  R  E  E  A  Q  V  A  A  R  A  Q  I  A  E
AACAATAAAGGCGGTTACTTTGGTAATGATGCCAACACAGGTTTCTCTGTCGAGTTTCAG        660
 N  N  K  G  G  Y  F  G  N  D  A  N  T  G  F  S  V  E  F  Q
CAGCCTTCTCCACGAGTTGTTGCCGCTGGTGTAATGGGAAATCTTGGTGCAGAGACTGCA        720
 Q  P  S  P  R  V  V  A  A  G  V  M  G  N  L  G  A  E  T  A
AATTCTTTGCAGGTTCAAGGTTCTAGTTTGCCTCTGAATGTGAATGGAGCTAGAACAACA        780
 N  S  L  Q  V  Q  G  S  S  L  P  L  N  V  N  G  A  R  T  T
TACCAGCAATCGCAACAGCAACAGCCAATCATGCCTAAGCAGCCTGGTTTTGGTTATGGA        840
 Y  Q  Q  S  Q  Q  Q  Q  P  I  M  P  K  Q  P  G  F  G  Y  G
ACACAAATGGGTCAGCTTAATAGTCCTGGGATAAGAGGTGGTGGTCTTGTGGGACTTGGA        900
 T  Q  M  G  Q  L  N  S  P  G  I  R  G  G  G  L  V  G  L  G
GATCAGTCTTTAACGAACAATGTGGGCTTTGTCCAAGGTGCTTCTGCTGCAATTCCTGGA        960
 D  Q  S  L  T  N  N  V  G  F  V  Q  G  A  S  A  A  I  P  G
GCTTTAGGCGTTGGTGCTGTGTCGCCTGTTACGCCATTGTCATCAGAAGGGATAGGGAAG       1020
 A  L  G  V  G  A  V  S  P  V  T  P  L  S  S  E  G  I  G  K
AGTAATGGTGATTCTTCATCACTCTCTCCGTCTCCTTACATGTTTAATGGTGGTGTGAGA       1080
 S  N  G  D  S  S  S  L  S  P  S  P  Y  M  F  N  G  G  V  R
GGTAGAAAGAGTGGCACTGTGGAGAAAGTTGTAGAGAGAAGGCAAAGGAGAATGATAAAG       1140
 G  R  K  S  G  T  V  E  K  V  V  E  R  R  Q  R  R  M  I  K
AACCGAGAATCAGCTGCAAGGTCCCGGGCCAGGAAAACAGGCTTACACCGTGGAGCTTGAA      1200
 N  R  E  S  A  A  R  S  R  A  R  K  Q  A  Y  T  V  E  L  E
GCTGAAGTTGCAAAGTTAAAGGAAGAGAATGACGAGTTACAACGAAAGCAGGCAAGGATC      1260
 A  E  V  A  K  L  K  E  E  N  D  E  L  Q  R  K  Q  A  R  I
ATGGAAATGCAAAAGAATCAGGAGACGGAGATGAGGAATCTTCTGCAAGGAGGTCCAAAG      1320
 M  E  M  Q  K  N  Q  E  T  E  M  R  N  L  L  Q  G  G  P  K
AAAAAGCTGAGGAGGACAGAGTCGGGACCTTGGTGAATCAATCAATGCCATCATACTTAG      1380
 K  K  L  R  R  T  E  S  G  P  W  *
TTTCTGTAGATAAATGACATCCCACTTAGGTGTTTTAGTTGAATTAGACTTAATAGAGAA      1440
GAGCTTTCATCGTTTATATTGTAAGCTCTCTCCATATATGTTATGTTTTTTACATACACA      1500
GGATCATCAGAATCTCTTTTTGCTTTATTTAGACCAAGAATTTTGTGTGTGTTTCTCGTTG     1560
TTGTTTGTCGTTGTCGCTATTAAACCTCAAAATGTACTTTCTTGATCTTGGAGTTACCAA     1620
TTTTGAAGAATTGAAGTGTTGTTTGGTTAAAAAA                                1654
```

FIG.2B

```
GAAGCTTGATCCTCCTAGTTGTACGAAAGCTTGAGTAATGGGGTCTAGATTAAACTTCAA          60
                                         M  G  S  R  L  N  F  K
GAGCTTTGTTGATGGTGTGAGTGAGCAGCAGCCAACGGTGGGGACTAGTCTTCCATTGAC         120
 S  F  V  D  G  V  S  E  Q  Q  P  T  V  G  T  S  L  P  L  T
TAGGCAGAACTCTGTGTTCTCGTTAACCTTTGATGAGTTTCAGAACTCATGGGGTGGTGG         180
 R  Q  N  S  V  F  S  L  T  F  D  E  F  Q  N  S  W  G  G  G
AATTGGGAAAGATTTTGGGTCTATGAACATGGATGAGCTCTTGAAGAACATTTGGACTGC         240
 I  G  K  D  F  G  S  M  N  M  D  E  L  L  K  N  I  W  T  A
AGAGGAAAGTCATTCAATGATGGGAACAATACCAGTTACACCAACATCAGCAATGGTAA         300
 E  E  S  H  S  M  M  G  N  N  T  S  Y  T  N  I  S  N  G  N
TAGTGGAAACACTGTTATTAACGGCGGTGGTAACAACATTGGTGGGTTAGCTGTTGGTGT         360
 S  G  N  T  V  I  N  G  G  G  N  N  I  G  G  L  A  V  G  V
GGGAGGAGAAAGTGGTGGTTTTTTCACTGGTGGGAGTTTGCAGAGACAAGGTTCACTTAC         420
 G  G  E  S  G  G  F  F  T  G  G  S  L  Q  R  Q  G  S  L  T
CTTGCCTCGGACGATTAGTCAGAAAAGGGTTGATGATGTCTGGAAGGAGCTGATGAAGGA         480
 L  P  R  T  I  S  Q  K  R  V  D  D  V  W  K  E  L  M  K  E
GGATGACATTGGAAATGGTGTTGTTAATGGTGGGACAAGCGGAATTCCGCAGAGGCAACA         540
 D  D  I  G  N  G  V  V  N  G  G  T  S  G  I  P  Q  R  Q  Q
AACGCTGGGAGAGATGACTTTGGAGGAGTTTTTGGTCAGGGCTGGTGTGGTTAGGGAAGA         600
 T  L  G  E  M  T  L  E  E  F  L  V  R  A  G  V  V  R  E  E
ACCTCAACCGGTGGAGAGTGTAACTAACTTCAATGGCGGATTCTATGGATTTGGCAGTAA         660
 P  Q  P  V  E  S  V  T  N  F  N  G  G  F  Y  G  F  G  S  N
TGGAGGTCTTGGGACAGCTAGTAATGGGTTTGTTGCAAACCAACCTCAAGATTTGTCAGG         720
 G  G  L  G  T  A  S  N  G  F  V  A  N  Q  P  Q  D  L  S  G
AAATGGAGTAGCGGTGAGACAGGATCTGCTGACTGCTCAAACTCAGCCACTACAGATGCA         780
 N  G  V  A  V  R  Q  D  L  L  T  A  Q  T  Q  P  L  Q  M  Q
                                          ‾  ‾  ‾  ‾  ‾  ‾  ‾
GCAGCCACAGATGGTGCAGCAGCCACAGATGGTGCAGCAGCCGCAACAACTGATACAGAC         840
 Q  P  Q  M  V  Q  Q  P  Q  M  V  Q  Q  P  Q  Q  L  I  Q  T
 ‾  ‾  ‾  ‾  ‾  ‾  ‾  ‾  ‾  ‾  ‾  ‾  ‾  ‾  ‾  ‾  ‾  ‾  ‾  ‾
GCAGGAGAGGCCTTTTCCCAAACAGACCACTATAGCATTTTCCAACACTGTTGATGTGGT         900
 Q  E  R  P  F  P  K  Q  T  T  I  A  F  S  N  T  V  D  V  V
 ‾
TAACCGTTCTCAACCTGCAACACAGTGCCAGGAAGTGAAGCCTTCAATACTTGGAATTCA         960
 N  R  S  Q  P  A  T  Q  C  Q  E  V  K  P  S  I  L  G  I  H
TAACCATCCTATGAACAACAATCTACTGCAAGCTGTCGATTTTAAAACAGGAGTAACGGT        1020
 N  H  P  M  N  N  N  L  L  Q  A  V  D  F  K  T  G  V  T  V
TGCAGCAGTATCTCCTGGAAGCCAGATGTCACCTGATCTGACTCCAAAGAGCGCCCTGGA        1080
 A  A  V  S  P  G  S  Q  M  S  P  D  L  T  P  K  S  A  L  D
TGCATCTTTGTCCCCTGTTCCTTACATGTTTGGGCGAGTGAGAAAAACAGGTGCAGTTCT        1140
 A  S  L  S  P  V  P  Y  M  F  G  R  V  R  K  T  G  A  V  L
GGAGAAAGTGATTGAGAGAAGGCAAAAAAGGATGATAAAGAATAGGGAATCAGCTGCAAG        1200
 E  K  V  I  E  R  R  Q  K  R  M  I  K  N  R  E  S  A  A  R
                    ‾  ‾  ‾  ‾  ‾  ‾  ‾  ‾  ‾  ‾  ‾  ‾  ‾  ‾
ATCCCGCGCTCGCAAGCAAGCTTATACGATGGAACTGGAAGCAGAAATTGCGCAACTCAA        1260
 S  R  A  R  K  Q  A  Y  T  M  E  L  E  A  E  I  A  Q  L  K
 ‾  ‾  ‾  ‾  ‾  ‾  ‾  ‾  ‾  ‾  ‾  ‾  ‾  ‾  ‾  ‾  ‾  ‾  ‾  ‾
AGAATTGAATGAAGAGTTGCAGAAGAAACAAGTTGAAATCATGGAAAAGCAGAAAAATCA        1320
 E  L  N  E  E  L  Q  K  K  Q  V  E  I  M  E  K  Q  K  N  Q
 ‾  ‾  ‾  ‾  ‾  ‾  ‾  ‾  ‾  ‾  ‾  ‾  ‾  ‾  ‾  ‾  ‾  ‾  ‾  ‾
GCTTCTGGAGCCTCTGCGCCAGCCATGGGGAATGGGATGCAAAAGGCAATGCTTGCGAAG        1380
 L  L  E  P  L  R  Q  P  W  G  M  G  C  K  R  Q  C  L  R  R
GACATTGACGGGTCCCTGGTAGAGCTTATAATGGCGTCTAAGGAACCCAACAAAGCGCCG        1440
 T  L  T  G  P  W  *
AAGTTATAGAACAACTCAGAAGATAGAAAGCTAGCTTTGTACGTAGTTTAGGCAGGTTCT        1500
GTGGGTGATTGTAAATCTTGAAGTGTGGCGGATTTGACAGAGATAGATAAACACATATCT        1560
GTTCTATTTTCCTAAATCTTTTGGTTTTATCTTCCTGATGTAATGGATCTTTATCATTTG        1620
TCTTGAACATCTTTGTGACTTAACCAGAGTGAATTTATCTTGTATCTAAAAAAAAAAAAA        1680
AAAAA                                                              1685
```

FIG.2C

```
ATTTGAACAAGGGTTTTAGGGCTTGGATGCTTTGTTTTCATTGAAAAAGAAGTAGAAGGA      60
GTGTATACAAGGATTATGGGAACTCACATCAATTTCAACAACTTAGGAGGTGGTGGTCAT     120
              M  G  T  H  I  N  F  N  N  L  G  G  G  H
CCTGGAGGGGAAGGGAGTAGTAACCAGATGAAGCCAACGGGTAGTGTCATGCCCTTGGCT     180
 P  G  G  E  G  S  S  N  Q  M  K  P  T  G  S  V  M  P  L  A
AGGCAGTCCTCGGTCTACTCCCTTACCTTTGATGAGTTACAGAACACACTAGGTGGACCG     240
 R  Q  S  S  V  Y  S  L  T  F  D  E  L  Q  N  T  L  G  G  P
GGAAAAGATTTCGGGTCGATGAACATGGATGAACTCCTGAAGAGCATATGGACTGCTGAG     300
 G  K  D  F  G  S  M  N  M  D  E  L  L  K  S  I  W  T  A  E
GAAGCTCAGGCCATGGCCATGACTTCTGCGCCAGCTGCTACAGCGGTAGCGCAACCTGGT     360
 E  A  Q  A  M  A  M  T  S  A  P  A  A  T  A  V  A  Q  P  G
GCTGGTATCCCACCCCCAGGTGGGAATCTCCAGAGGCAAGGTTCGTTGACGTTGCCTAGA     420
 A  G  I  P  P  P  G  G  N  L  Q  R  Q  G  S  L  T  L  P  R
ACAATTAGTCAGAAGACTGTTGATGAGGTGTGGAAATGTTTGATCACCAAGGATGGTAAT     480
 T  I  S  Q  K  T  V  D  E  V  W  K  C  L  I  T  K  D  G  N
ATGGAAGGTAGCAGCGGAGGCGGTGGTGAGTCGAATGTGCCTCCTGGAAGGCAACAGACT     540
 M  E  G  S  S  G  G  G  G  E  S  N  V  P  P  G  R  Q  Q  T
TTAGGGGAAATGACACTTGAAGAATTTCTGTTCCGTGCTGGGGTTGTAAGAGAAGATAAC     600
 L  G  E  M  T  L  E  E  F  L  F  R  A  G  V  V  R  E  D  N
TGTGTTCAACAGATGGGTCAGGTCAACGGAAACAATAACAATGGGTTTTATGGTAACAGC     660
 C  V  Q  Q  M  G  Q  V  N  G  N  N  N  N  G  F  Y  G  N  S
ACTGCTGCTGGCGGCTTAGGTTTTGGATTTGGTCAGCCAAATCAAAACAGCATAACATTC     720
 T  A  A  G  L  G  F  G  F  G  Q  P  N  Q  N  S  I  T  F
AATGGTACTAATGATTCTATGATCTTGAATCAGCCACCTGGTTTAGGGCTCAAAATGGGT     780
 N  G  T  N  D  S  M  I  L  N  Q  P  P  G  L  G  L  K  M  G
GGAACAATGCAGCAGCAACAACAACAACAGCAGTTGCTTCAGCAGCAACAACAGCAGATG     840
 G  T  M  Q  Q  Q  Q  Q  Q  Q  Q  L  L  Q  Q  Q  Q  Q  M
CAGCAGCTGAATCAGCCTCATCCACAGCAGCGGCTGCCTCAAACCATTTTTCCTAAACAA     900
 Q  Q  L  N  Q  P  H  P  Q  Q  R  L  P  Q  T  I  F  P  K  Q
GCAAACGTAGCATTTTCTGCGCCTGTGAATATAACCAACAAGGGTTTTGCTGGGGCTGCA     960
 A  N  V  A  F  S  A  P  V  N  I  T  N  K  G  F  A  G  A  A
AATAATTCTATCAACAATAATAATGGATTAGCTAGTTACGGAGGAACCGGGGTCACTGTT    1020
 N  N  S  I  N  N  N  N  G  L  A  S  Y  G  G  T  G  V  T  V
GCAGCAACTTCTCCAGGAACAAGCAGCGCAGAAAATAATTCTTTATCACCAGTTCCGTAT    1080
 A  A  T  S  P  G  T  S  S  A  E  N  N  S  L  S  P  V  P  Y
GTGCTTAATCGAGGACGAAGAAGCAATACAGGTCTAGAGAAGGTTATCGAGAGGAGGCAA    1140
 V  L  N  R  G  R  R  S  N  T  G  L  E  K  V  I  E  R  R  Q
AGGAGAATGATCAAGAATCGGGAATCAGCTGCTAGATCAAGAGCTCGAAAGCAGGCTTAT    1200
 R  R  M  I  K  N  R  E  S  A  A  R  S  R  A  R  K  Q  A  Y
ACATTGGAACTGGAAGCCGAAATTGAAAAGCTCAAGAAAACGAATCAAGAACTGCAGAAA    1260
 T  L  E  L  E  A  E  I  E  K  L  K  K  T  N  Q  E  L  Q  K
AAACAGGCTGAAATGGTGGAAATGCAGAAGAATGAGCTGAAAGAAACGTCGAAGCGACCG    1320
 K  Q  A  E  M  V  E  M  Q  K  N  E  L  K  E  T  S  K  R  P
TGGGGCAGCAAAAGGCAATGCTTGAGAAGGACATTAACCGGACCATGGTGAAGGATGAAG    1380
 W  G  S  K  R  Q  C  L  R  R  T  L  T  G  P  W  *
CAACAAGAACGGATGAACCAGACTCCTAGCTTGGGATTAATGTAATAGGATAGTGCTACC    1440
TGTACAGGAGATTAAGAGAAATTGAGTGAAAGATCTAGGTTACAGAGTAGGAGAGAGTTT    1500
TCATTATGAATAAATGACATTTTGTGCCCTGACCTTTGTTAGTTTAGGTTTAGATTATCC    1560
TCTGTTATTGACTTATTGTGCTTTCTGGTTGTTAGGGTTTCTAAAAGACATAGTTGTTTA    1620
TATATATGTCTGACTTTGTATTCCGGATTTGGTTCTCTTGTGTCATTAACTTGGGTTTAG    1680
CCATTATTACTTAAGAGTGGCAACGAAATCAAAAAAAAAAAAAAAAAAAAAAAAAAAAAA    1740
A                                                              1741
```

FIG.2D

```
ABF1    1 MGTHIDINNLGGDTSRGNESK----------PLARQSSLYSLTFDELQSTLGE-PGKDF    48
ABF4    1 MGTHINFNNLGGGGHPGGEGSSNQMKPTGSVMPLARQSSVYSLTFDELQNTLGG-PGKDF    59
ABF3    1 MGSRLNFKSFVDGVSEQQPTVG-------TSLPLTRQNSVFSLTFDEFQNSWGGGIGKDF    53
ABF2    1 MDGSMNLGNEPPG--DGGGGGG----------LTRQGSIYSLTFDEFQSSV----GKDF    43

ABF1   49 GSMNMDELLKNIWTAEDTQAFMTTTS-----------------------SVAAPGPSG    83
ABF4   60 GSMNMDELLKSIWTAEEAQAMAMTSAPAA---------------------TAVAQPGAGI    98
ABF3   54 GSMNMDELLKNIWTAEEESHSMMGNNTSYTNISNGNSGNTVINGGGNNIGGLAVGVGGESG   113
ABF2   44 GSMNMDELLKNIWSAEETQAMASGVVP-----------------------VLGGGQE-    77

ABF1   84 FVPGGNGLQRQGSLTLPRTLSQKTVDEVWKYLNSK----EGSNGNTGTDALE--------   131
ABF4   99 PPPGGN-LQRQGSLTLPRTISQKTVDEVWKCLITKDGNMEGSSGGGGESNVPPG------   151
ABF3  114 GFFTGGSLQRQGSLTLPRTISQKRVDDVWKELMKED-DIGNGVVNGGTSGIPQ-------   165
ABF2   78 ----GLQLQRQGSLTLPRTLSQKTVDQVWKDLSKVG---SSGVGGSNLSQVAQAQSQSQS   130

ABF1  132 -RQQTLGEMTLEDFLLRAGVVKEDNTQQ-----NENSSSGFYANNGAAG---LEFGFGQP   182
ABF4  152 -RQQTLGEMTLEEFLFRAGVVREDNCVQQMGQVNGNNNNGFYGNSTAAGG--LGFGFGQP   208
ABF3  166 -RQQTLGEMTLEEFLVRAGVVREEPQPVES---VTNFNGGFYGFGSNGGLGTASNGFVAN   221
ABF2  131 QRQQTLGEVTLEEFLVRAGVVREEAQVAARAQIAENNKGGYFGNDANTG---FSVEFQQP   187

ABF1  183 NQNSISFNGNNSSMIMNQAPGLGLKVGGTMQQQQQQP---------HQQQLQQPH--QRLP   231
ABF4  209 NQNSITFNGTNDSMILNQPPGLGLKMGGTMQQQQQQQQLLQQQQQQMQQLNQPHQQRLP   268
ABF3  222 QPQDLSGNG----VAVRQDLLTAQTQPLQMQQPQMVQ--------QPQMVQQPQQLIQTQ   269
ABF2  188 SPR-VVAAG-----VMGN-LGAETANSLQVQGSSLP--------LNVNGARTTYQQSQQQ   232

ABF1  232 PTIFPKQANVTFAAPVNMVNRG------------LFETSADGPANSN---------MGGAG   271
ABF4  269 QTIFPKQANVAFSAPVNITNKG------------FAGAANNSINNNNGLAS----YGGTG   312
ABF3  270 ERPFPKQTTIAFSNTVDVVNRSQPATQCQEVKPSILGIHNHPMNNNLLQAV----DFKTG   325
ABF2  233 QPIMPKQPGFGYGTQMGQLNSPGIRGG------GLVGLGDQSLTNNVGFVQGASAAIPGA   286

ABF1  272 GTVTATSPG---------TSSAENNTWSSPVPYVFG---RGRRSNTGLEKVVERRQKRMI   319
ABF4  313 VTVAATSPG---------TSSAENNSLS-PVPYVLN---RGRRSNTGLEKVIERRQRRMI   359
ABF3  326 VTVAAVSPGSQMSPD-LTPKSALDASLS-PVPYMFG---RVRKTGAVLEKVIERRQKRMI   380
ABF2  287 LGVGAVSPVTPLSSEGIGKSNGDSSSLS-PSPYMFNGGVRGRKS-GTVEKVVERRQRRMI   344

ABF1  320 KNRESAARSRARKQAYTLELEAEIESLKLVNQDLQKKQAEIMKTHNSELKEFSKQPP-LL   378
ABF4  360 KNRESAARSRARKQAYTLELEAEIEKLKKTNQELQKKQAEMVEMQKNELKETSKRP--WG   417
ABF3  381 KNRESAARSRARKQAYTMELEAEIAQLKELNEELQKKQVEIMEKQKNQLLEPLRQPWGMG   440
ABF2  345 KNRESAARSRARKQAYTVELEAEVAKLKEENDELQRKQARIMEMQKNQETEMRNLLQ--G   402

ABF1  379 AKRQCLRRTLTGPW   392
ABF4  418 SKRQCLRRTLTGPW   431
ABF3  441 CKRQCLRRTLTGPW   454
ABF2  403 GPKKKLRRTESGPW   416
```

FIG. 3

ABRE    aattccGGA<u>CACGTGGC</u>Gtaagct
mABRE   aattccGGACctacaGCCtaagct

```
                                    IA (gACACGTG^G/+C)
  4R.             GGATCCTGTCGTGGGGGACACGTGGCATACGAGGCGAATTC
 11R.             GGATCCTGTCGGGGGACACGTGGCGCTAACGAGGCGAATTC
 12R.              GGATCCTGTCGGGGACACGTGGCGCAACACGAGGCGAATTC
 20R.              GGATCCTGTCGGGGACACGTGGCCCACCCGGAGGCGAATTC
 39R.              GGATCCTGTCGGGGACACGTGGCACAAATAGAGGCGAATTC
  9R.             GGATCCTGTCGTCAATGGACACGTGGCTAGAGGCGAATTC
 10R.               GGATCCTGTCGTCGGACACGTGGCACGAAGAGGCGAATTC
 32.              GAATTCGCCTCGACAGGACACGTGGCACGCGACAGGATCC
 25R.             GGATCCTGTCGATCAATGGACACGTGGCAGAGGCGAATTC
 21.                 GAATTCGCCTCGGTGACACGTGGCTTGACCGACAGGATCC              (17)
 40R.            GGATCCTGTCGGAAGTGGTGACACGTGGCGAGGCGAATTC
 35.              GAATTCGCCTCAAGAGGTGACACGTGGCACGACAGGATCC
 26R.                GGATCCTGTCGCGACACGTGGCTGTTAGTGAGGCGAATTC
 15.              GAATTCGCCTCTAAGGAACACGTGGCCCGCGACAGGATCC
 36.              GAATTCGCCTCCGGGCGGAACACGTGGCACGACAGGATCC
 19R.             GGATCCTGTCGCGTGGGTACACGTGGCCCGAGGCGAATTC
  6R.            GGATCCTGTCGCGGTCTTTATGACACGTGGAGGCGAATTC

38.                 GAATTCGCCTCGGACACGTGTCCCGATCCCGACAGGATCC
 45.              GAATTCGCCTCTAAGGCGGGACACGTGTCCGACAGGATCC              (3)
 42.                GAATTCGCCTCTGACACGTGTCAGTCCCACGACAGGATCC

IAA (CCACGTGGC)
  7.              GAATTCGCCTCGGGGGCCACGTGGCTTCCGCGACAGGATCC
 17.              GAATTCGCCTCTTCGATGGCCACGTGGCGCGACAGGATCC
 43.              GAATTCGCCTCTTAAGTGGCCACGTGGCGCGACAGGATCC
 22.              GAATTCGCCTCTCACGAGGCCACGTGGCACGACAGGATCC
 16.              GAATTCGCCTCCGTGGCGCCACGTGGCCGCGACAGGATCC
 23.              GAATTCGCCTCAATGCACCGCCACGTGGCCGACAGGATCC
 30.              GAATTCGCCTCCCTGACTGCCACGTGGCACGACAGGATCC              (13)
 37.              GAATTCGCCTCCAAGCGTTCGCCACGTGGCGACAGGATCC
 28.               GAATTCGCCTCTTTGTCCACGTGGCCCACCGACAGGATCC
 18.              GAATTCGCCTCTAGACCGTCCACGTGGCCCGACAGGATCC
 14.              GAATTCGCCTCTACCACGTGGCACACCGTCGACAGGATCC
 29R.             GGATCCTGTCGGCTACCACGTGGCAAGAAGAGGCGAATTC
 34.              GAATTCGCCTCCCTTAGCACCACGTGGCACGACAGGATCC

IB (GNTGACGTG^G/+C)
  1R.             GGATCCTGTCGGTTCGATGACGTGGCGAGGAGGCGAATTC
 33R.             GGATCCTGTCGGCTTGATGACGTGGCCACGAGGCGAATTC
 44.              GAATTCGCCTCCTTGATGACGTGGCACCACGACAGGATCC              (5)
  3R.             GGATCCTGTCGTGGCTGACGTGGCACTAGGAGGCGAATTC
  8R.             GGATCCTGTCGGCGCGTGGTGACGTGGCCGAGGCGAATTC

48R.             GGATTCTGTCGATTCGGTGACGTGTCCCGGAGGCGAATTC
  5.              GAATTCGCCTCTGGCTGCTGACGTGTCCCCGACAGGATCC              (2)
 27R.                GGATCCTGTCGACGTGGCAACTTGAACGCGAGGCGAATTC              (2)
  2R.             GGATCCTGTCGTTGGGCTTACGTGGCAGCGAGGCGAATTC

49.              GAATTCGCCTCGCCCTGAAGTGGACAGCGCGACAGGATCC              (1)

II (CGCGTG)
 24.              GAATTCGCCTCCCGTCCGCGTGGCAGCAGCGACAGGATCC              (1)

8RB.            GGATCCTGTCGGCGCGTGGTGACGTGGCCGAGGCGAATTC
 19RB.            GGATCCTGTCGCGTGGGTACACGTGGCCCGAGGCGAATTC              (3)
 32RB.            GGATCCTGTCGCGTGCCACGTGTCCTGTCGAGGCGAATTC
```

FIG.5B

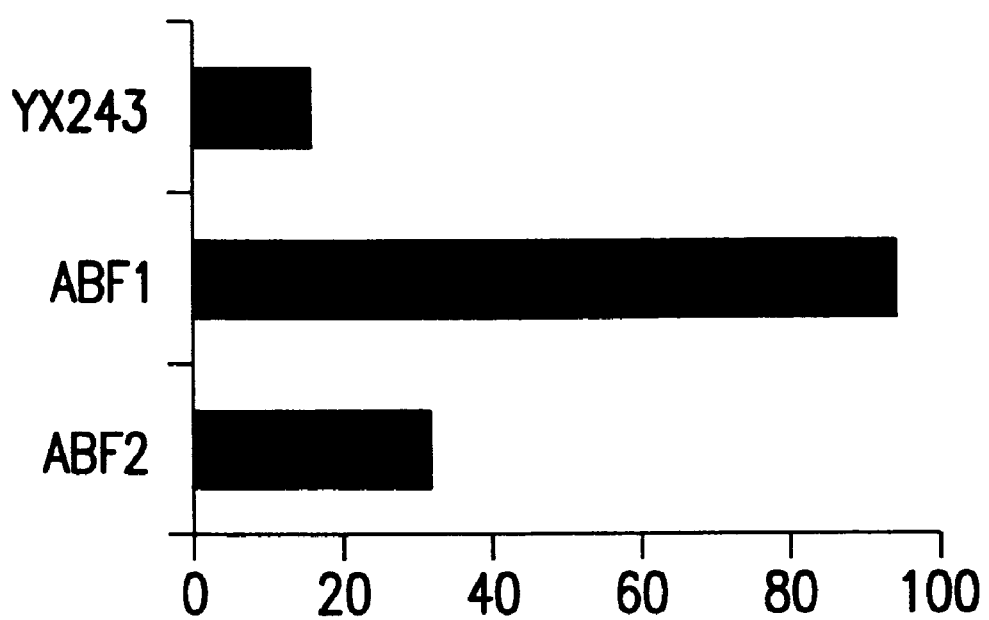
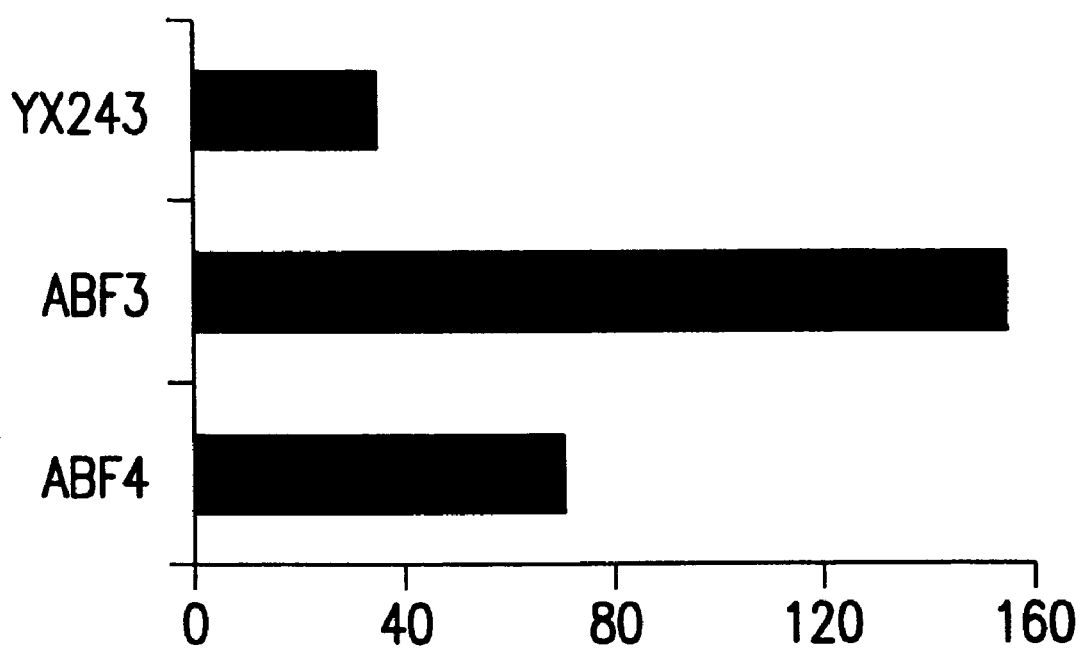
FIG. 7

```
              BASIC REGION                    ZIPPER REGION
ABF1    LEKVVE RRQKRMIKNRESAARSRARK QAY TLELEAEIESLKLVNQDLQKKQAEIMKTHNS-
ABF4    LEKVIE RRQRRMIKNRESAARSRARK QAY TLELEAEIEKLKKTNQELQKKQAEMVEMQKN-
ABF3    LEKVIE RRQKRMIKNRESAARSRARK QAY TMELEAEIAQLKELNEELQKKQVEIMEKQKN-
ABF2    VEKVVE RRQRRMIKNRESAARSRARK QAY TVELEAEVAKLKEENDELQRKQARIMEMQKN-

DPBF1   VEKVVE RRQRRMIKNRESAARSRARK QAY TVELEAELNMLKEENAQLKQALAEIERKRKQ-
DPBF2   MEKTVE RRQKRMIKNRESAARSRARK QAY THELENKVSRLEEENERL-RREKEVEKVIPWV
DPBF3   IEKTVE RRQKRMIKNRESAARSRARK QAY THELENKISRLEEENELL-KRQKEVGMVLPSA mlip15  NDTTDE RKRKRMLSNRESARRSRARK QQR LEELVAEVARLQAENAATQARTAALERDLGR-
EMBP1   MDEREL KRERRKQSNRESARRSRLRK QQE CEELAQKVSELTAANGTLRSELDQLKKDCKT-
OSBZ8   KDDKES KRERRKQSNRESARRSRLRK QAE TEELARKVELLTAENTSLRREISRLTESSKK-
GBF3    QNEREL KRERRKQSNRESARRSRLRK QAE TEELARKVEALTAENMALRSELNQLNEKSDK-
TAF1    QNEREL KREKRKQSNRESARRSRLRK QAE AEELAIRVQSLTAENMTLKSEINKLMENSEK-
```

FIG. 8A

NUCLEIC ACID MOLECULE ENCODING ABSCISIC ACID RESPONSIVE ELEMENT-BINDING RACTOR 4

This application is a division of application Ser. No. 09/416,050 filed Oct. 12, 1999.

BACKGROUND OF THE INVENTION

This invention relates to a family of novel transcription factors that bind to various abscisic acid responsive elements (ABREs), more particularity, factors named as ABFs (ABRE-Binding Factors) isolated by yeast one-hybrid screening of anArabidopsis cDNA expression library using a prototypical ABRE (SEQ ID NO: 9; GGACACGTGGCG).

Abscisic acid (ABA) is one of the major plant hormones that plays an important role during plant growth and development (Leung and Giraudat, 1998). The hormone controls several physiological processes during seed development and germination. During vegetative growth, ABA is known to mediate responses to various adverse environmental conditions such as drought, high salt and cold/freezing (Shinozaki and Yamaguchi-Shinozaki, 1996).

One of the ABA-mediated responses to various environmental stresses is the induced expression of a large number of genes, whose gene products are involved in the plant's adaptation to the stresses (Ingram and Bartels, 1996). ABA responsive elements (ABREs), i.e., cis-regulatory elements that mediate the ABA-modulated gene expression, have been identified from the promoter analysis of ABA-regulated genes (reviewed in Busk and Pages, 1998). One class of the ABREs includes elements that share a PyACGTGGC (Py indicates C or T) consensus sequence, which can be considered a subset of a larger group of cis-elements known as "G-box" (Menkens et al., 1995). Another class of ABREs, known as "coupling elements (CE)" or "motif III", shares a CGCGTG consensus sequence. Both classes of ABREs, here, referred to as G/ABRE (G-box-like ABRE) and C/ABRE (CE-like ABRE), respectively, are almost ubiquitous in the promoter regions of ABA responsive genes of both monocotyledonous and dicotyledonous plants.

A number of basic leucine zipper (bZIP) class DNA-binding proteins are known to interact with the ABREs (Busk and Pages, 1998). EmBP1 and TAF1 have been isolated based on their in vitro binding activity to G/ABREs. GBF3, originally identified as one of the G-box binding factors (GBFs) involved in the light regulation of a ribulose bisphosphate carboxylase gene (Schindler et al., 1992), has been cloned using the ABA-responsive, G-box element of a Arabidopsis Adh1 gene. Recently, a family of embryo-specific factors has been reported that can recognize both G/ and C/ABREs (Kim and Thomas, 1998; Kim et al., 1997). Other factors binding to G-box have also been described (Foster et al., 1994).

Although ABRE-binding factors have been known for some time, several observations suggest that hitherto unidentified factors are involved in ABA-regulated gene expression during stress response, especially in vegetative tissues. ABA-induction of rice rab16A and Arabidopsis rd29B genes requires de novo protein synthesis (Nakagawa et al., 1996; Yamaguchi-Shinozaski and Shinozaki, 1994), suggesting the involvement of ABA-inducible factors. In vivo binding of ABA-inducible factors has been demonstrated in maize rab17 gene (Busk et al., 1997). In the case of rab16B gene, currently unknown, C/ABRE-binding factor(s) has been suggested to mediate ABA response through the motif III (Ono et al., 1996). Furthermore, it has been well established by genetic studies that different ABA signaling pathways operate in seeds and in vegetative tissues, respectively (Leung and Giraudat, 1998), and tissue-specific ABRE-binding activities have been demonstrated (Pla et al., 1993). None of the source materials used in the previous protein-DNA interaction clonings, however, were ABA- or stress-treated young plant tissues, and thus, inducible factors that may be critical for the ABA-mediated stress response during vegetative growth phase may have been missed so far.

Numerous stress responsive genes involved in plant's adaptation to various environmental stresses are regulated by ABA through G/ABREs or C/ABREs (Ingram and Bartels, 1996). Therefore, overexpression of ABRE-binding transcription factors will result in the activation of these stress-inducible genes and thus enhanced stress tolerance. Hence, once isolated, the ABRE-binding factors will be suitable for the generation of transgenic plants that are tolerant to multiple environmental stresses. Feasibility of manipulating transcription factors for the improved stress tolerance has been demonstrated by others recently (Jaglo-Ottosen et al., 1998; Kasuga et al., 1999).

SUMMARY OF THE INVENTION

This invention relates to a family of novel transcription factors that bind to various ABREs. The factors, named as ABFs (ABRE-Binding Factors), were isolated by yeast one-hybrid screening of an Arabidopsis cDNA expression library using a prototypical ABRE (SEQ ID NO: 9; GGACACGTGGCG). ABFs are bZIP class transcription factors that can bind to both G/ABREs and C/ABREs. Expression of ABFs is inducible by ABA and various stress treatments, and they can transactivate an ABRE-containing reporter gene in yeast. Thus, ABFs have potential to activate a large number of ABA/stress responsive genes and thus can be used to generate transgenic plants that are tolerant to multiple environmental stresses.

BRIEF DESCRIPTION OF THE DRAWINGS

FIGS. 2A–2D Nucleic and deduced amino acid sequences of ABFs. Nucleic acid sequences of ABFs are presented together with deduced amino acid sequences. The bZIP and the glutamine-rich regions are underlined. FIG. 2A: ABF1 (SEQ ID NOS: 1 and 2), FIG. 2B: ABF2 (SEQ ID NOS: 3 and 4), FIG. 2C: ABF3 (SEQ ID NOS: 5 and 6) and FIG. 2D: ABF4(SEQ ID NOS: 7 and 8) correspond to clones 1, 2, 11, and 19, respectively.

FIG. 3. Alignment of the deduced amino acid sequences of ABFs. The deduced amino acid sequences of ABFs (SEQ ID NO: 2, SEQ ID NO: 4, SEQ ID NO: 6, SEQ ID NO: 8) are aligned together. The basic region and the leucine repeats are shown by a thick line and arrowheads, respectively. The small arrow indicates the arginine and the lysine residues within the basic regions that are discussed in the text. Regions highly conserved are highlighted. #, CaMK II sites. +, CK II sites.

FIG. 4A, ABF1 binding to a G/ABRE. An oligonucleotide (ABRE) containing the EM1a element (SEQ ID NO: 11) was employed as a probe in a mobility shift assay. FIG. 4B, ABF1 binding to a C/ABRE. An oligonucleotide containing the hex-3 sequence (SEQ ID NO: 13) was employed as a probe. In each assay, 1 μg of recombinant ABF1 was used. Lanes 1, probe only (−); 2, probe and ABF1 (+); 3 and 4, 100-fold and 200-fold molar excess of specific competitors (ABRE, SEQ ID NO: 13 and hex-3, SEQ ID NO: 13), respectively; 5 and 6, 100-fold and 200-fold molar excess of a mutated oligonucleotide mABRE, SEQ ID NO: 12 and mhex-3, SEQ ID NO; 14) as competitors, respectively. Sequences of oligonucleotides are shown at the bottom of each figure and shifted bands are indicated by arrowheads.

FIGS. 5A–5B. Binding site selection assay. FIG. 5A, binding site selection assay. Top; Probes (P0 to P5) after each round of selection were amplified and used in EMSA. 1.5 μg of ABF1 was used. Only the top part of the gel containing the shifted bands is shown. Bottom; EMSA of P5 probe DNA. P5 probe DNA was employed in EMSA and titrated with increasing amount (μg) of ABF1. Arrowheads denote shifted bands. The band shown by * is probably an artifact resulting from secondary structure formation of palindromic sequences in the selected sequences. FIG 5B, selected sequences. The selected sequences (SEQ ID NOS: 33–79) are aligned and grouped according to their consensus sequences shown in parentheses. The nucleotides highly conserved within each group are in bold, and those 100% conserved are underlined. G/ABRE elements flanking the C/ABRE core of group II sequences are in italics and underlined. The number of selected sequences in each group is indicated in the parentheses on the right.

FIG. 7. Transactivation assay of ABFs. Transactivational function of ABFs was tested by using a yeast system. ABFs were expressed in yeast that harbored an ABRE-containing lacZ reporter gene. The β-galactosidase activity was then assayed and indicated as Miller units. For each construct, 5 different transformants were assayed in duplicates. YX243, control vector without any inserts.

FIGS. 8A–8B. Phylogenetic analysis of ABRE-binding bZIP factors. FIG. 8A, bZip regions of the ABRE factors mentioned in the text (SEQ ID NO: 80, SEQ ID NO: 81, SEQ ID NO: 82, SEQ ID NO: 83). mlip15 is a maize bZIP factor induced by low-temperature (SEQ ID NO: 28; Kusano et al., 1995). Conserved amino acids are highlighted, and the leucine residues in the "zipper" regions are underlined (SEQ ID NOs: 2, 4, 6, 8 and DPBF1, SEQ ID NO: 25; DPBF2, SEQ ID NO: 26; DPBF3; SEQ ID NO: 27; mlip15, SEQ ID NO: 28; EMB1, SEQ ID NO: 29; OSBZ8, SEQ ID NO: 30; GBF3, SEQ ID NO: 31; TAF1, SEQ ID NO: 32-25-32). FIG. 8B, unrooted phylogenetic tree diagram. The bZIP regions shown in FIG. 8A were aligned and a tree diagram was constructed using CLUSTAL W algorithm.

DETAILED DESCRIPTION OF THE INVENTION

Materials and Methods

Figure 1:
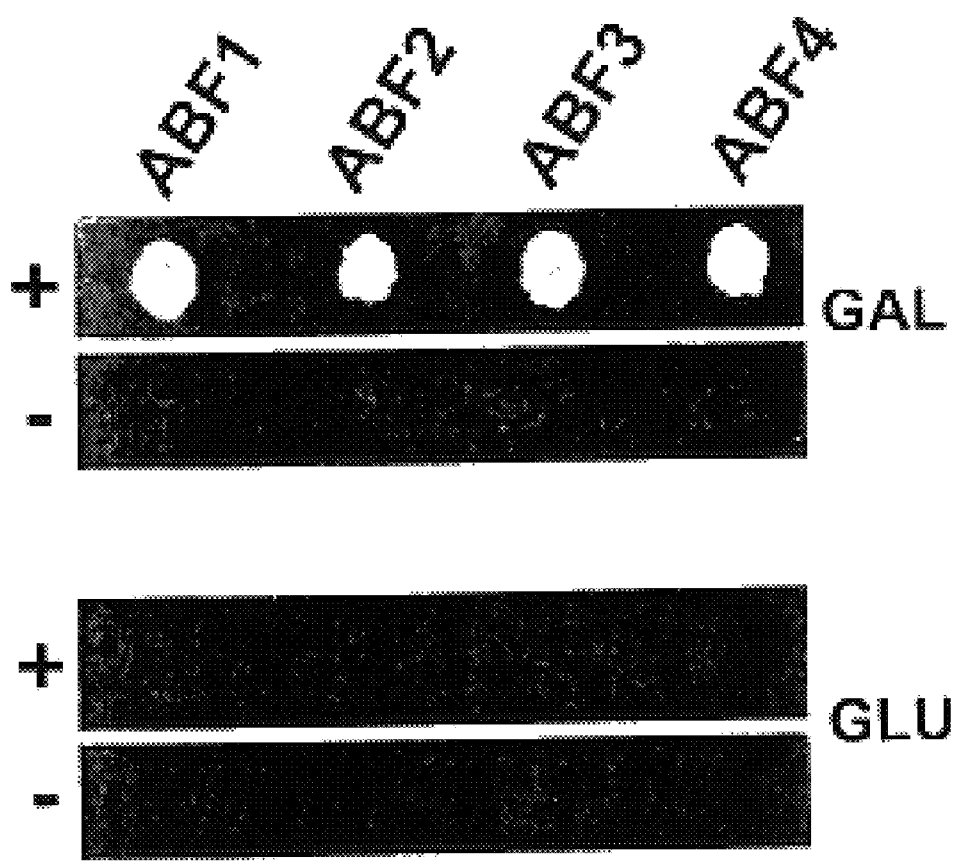
FIG. 1. Specificity of ABF binding. Binding specificity of ABFs. A reporter yeast containing a HIS3 reporter construct with (+) or without (−) the ABRE (a trimer of Em1a; SEQ ID NO: 10) was transformed with DNA from representative clones, and transformants were grown on either galactose (GAL) or glucose (GLU) medium lacking histidine.

Plant materials—*Arabidopsis thaliana* (ecotype Columbia) was grown at 22° C. on pots of soil (a 1:1 mixture of vermiculite and peat moss) irrigated with mineral nutrient solution (0.1% Hyponex) in 8 hr light/16 hr dark cycles. For RNA isolation, 4–5 weeks old plants were subject to various treatments, flash-frozen in liquid nitrogen and kept at −70° C. until needed. For ABA treatment, roots of plants were submerged, after the removal of soil, in a 100 μM ABA (Sigma, No A 1012) solution for 4 hr with gentle shaking. ABA solution was also sprayed intermittently during the incubation period. Salt treatment was performed in the same way, except that 250 mM NaCl solution was employed. For drought treatment, plants were withheld from water for two weeks before harvest, and left on the bench, after removing soil, for 1 hr just before collection. For cold treatment, plants were placed at 4° C. for 24 hr under dim light before harvest.

Yeast techniques, DNA manipulation and RNA gel blot analysis—Standard methods (Ausubel et al., 1994; Guthrie and Fink, 1991; Sambrook et al., 1989) were used in manipulating DNA and yeast. DNA sequencing was performed on ABI 310 Genetic Analyzer, according to the manufacturer's instruction. DNA sequence analysis was done with DNA Strider® and Generunr®, and BLAST algorithm (Altschul et al., 1990) was used for database search. Multiple sequence alignment and phylogenetic tree construction were performed with CLUSTAL W program (Thompson et al., 1994) available on the web (http://www2.ebi.ac.uk/clustalw).

RN0A was isolated according to Chomczynski and Mackey (1995) and further purified by LiCl precipitation followed by ethanol precipitation. For RNA gel blot analysis, 25 μg of total RNA was fractionated on 1.1% formaldehyde agarose gel, transferred to nylon membrane (Hybond-N+, Amersham) by "downward capillary transfer" method (25), and fixed using Stratagene's UV Crosslinker (Model 2400). Loading of equal amount of RNAs was confirmed by ethidium bromide staining. Hybridization was at 42° C. in 5X SSC (1×SSC is 0.15 M NaCl, 0.015 M sodium citrate), 5×Denhardt's solution (1×Denhardt's solution is 0.02% Ficoll, 0.02% PVP, 0.02% BSA), 1% SDS, 100 μml salmon sperm DNA, and 50% foramide for 24–30 hrs. Probes were prepared from the variable regions of ABFs. After hybridization, filters were washed twice in 2×SSC, 0.1% SDS at room temperature and three times in 0.2×SSC, 0.1% SDS for 10 min each at 65 ° C. Exposure time was 7–8 days. RT-PCR was performed employing the Access RT-PCR System (Promega) using 0.5 g of total RNA according to the manufacturer's instruction. Amplification after the first strand cDNA synthesis was 45, 35, 40 and 45 cycles for ABF1, 2, 3 and 4, respectively. ABF primers (sequences are available upon request) were from variable regions between the bZIP and the conserved regions. The actin primers used in the control reaction was from the Arabidopsis actin-1 gene (GenBank Accession No., M20016). Free of contaminating DNA in RNA samples was confirmed by using primer sets (ABF3 and actin) that flank introns.

cDNA library construction and yeast one-hybrid screening—Poly A(+) RNA was isolated from total RNAs prepared from ABA- or salt-treated Arabidopsis seedlings, using Qiagen's Oligotex resin. cDNA was synthesized from an equal mixture (6 μg total) of poly A(+) RNAs prepared from the -two sources of total RNAs employing a Stratagene's cDNA synthesis kit. cDNA was fractionated on a Sepharose CL-2B column, peak fractions containing cDNAs larger than 500 bp were pooled, and pooled cDNAs were ligated with pYESTrp2 (Invitrogen) predigested with Eco RI-Xho I. The ligation mixture was electroporated into *E.coli* DH10B cells. Titer of this original library was 5.4× $10^7$ cfu. Portion of the library ($2×10^7$) was plated on 15 cm plates at a density of 150,000 cfu/plate. Cells were suspended in LB after overnight growth at 37° C. on plates and pooled together. Finally, plasmid DNA was prepared from the collected cells.

pYC7-I and pSK1 (Kim and Thomas, 1998) were used as HIS3 and lacZ reporter plasmids, respectively. The G/ABRE reporter construct was prepared by inserting a trimer of Em1a element (SEQ ID NO: 9; Guiltinan et al., 1990) into the Sma I site of pYC7-I and the Xba I site of pSK1. In order to prepare reporter yeast, YPH 500 was transformed with the Stu I-digested pYC7-I reporter construct. Resulting Ura+ colonies were transformed with the pSK1 construct and maintained on a SC-LEU-URA medium. Screening of the library was performed as described (Kim and Thomas, 1998) except that transformed reporter yeast was grown on Gal/Raf/CM-HIS-LEU-TRP plates instead of Glu/CM-HIS-LEU-TRP plates. Putative positive clones from the screen were streaked on fresh Gal/Raf/CM-HIS-LEU-TRP plates to purify colonies. After β-galactosidase assay, well-isolated single colonies were patched on Glu/CM-LEU-TRP-URA plates to be kept as master plates. Galactose-dependency of the His$^+$/lacZ$^+$ phenotype of the purified isolates was examined subsequently by comparing their growth pattern and β-galactosidase activity on Gal/Raf/CM-HIS-LEU-TRP and Glu/CM-HIS-LEU-TRP dropout plates.

Analysis of positive clones—Yeast DNA was prepared from 1.5 ml of overnight cultures of the positive clones. PCR was performed with primers derived from the pYESTrp2 vector sequences flanking the inserts (pYESTrp forward and reverse primers). PCR products were digested with Eco RI, Hae III, or Alu I in order to group the cDNAs. For library plasmid rescue, yeast DNAs from representative clones were introduced into DH10B E.coli cells by electroporation. Plasmid DNAs used in DNA sequencing and confirmation experiments were isolated from these E.coli transformants by the alkaline lysis method. For the confirmation experiment shown in FIG. 1, plasmid DNAs thus isolated were re-introduced into the yeast containing pSK1 or ABRE-pSK1, transformants were kept on Glu/CM-LEU-TRP plates, and their growth was tested after spotting 5 μl of overnight cultures (1/50 dilutions) on Gal/Raff/CM-HIS-LEU-TRP or Glu/CM-HIS-LEU-TRP plates containing 2.5 mM 3-aminotriazole.

Isolation of full-length ABF3 and 4—A PCR approach was used to isolate the missing 5' portions of clone 11 and clone 19. Database search revealed that clone 11 was part of the BAC clone F28A23 of the Arabidopsis chromosome IV. On the other hand, the 5' portion of the clone 19 sequence was identical to the 3' region of an EST clone, 176F17T7. Based on the sequence information, 5' PCR primers (5'-GAAGCTTGATCCTCCTAGTTGTAC-3'; SEQ ID NO: 15 for clone 11 and 5'-ATTTGAACAAGGGTTTTAGGGC-3', SEQ ID NO: 16 for clone 19 were synthesized. 3' primers 5'-TTACAATCACCCACAGAACCTGCC-3'; SEQ ID NO: 17 and 5'-GATTTCGTTGCCACTCTTAA-3'; SEQ ID NO: 18, which are complementary to the 3'-most sequences of clones 11 and 19, respectively) were prepared using our sequence information. PCR was performed with Pwo polymerase (Boeringer Mannheim), using the primer sets and 1 μg of our library plasmid DNA. After 30 cycles of reaction, the DNA fragments corresponding to the expected size of the full-length clones were gel-purified and cloned into the PCR-Script vector (Stratagene). Several clones from each PCR product were then sequenced in their entirety. The fidelity of the full-length sequences was confirmed by comparing their sequences with each other and with those of the original partial clones and the genomic clones deposited later by the Arabidopsis Genome Initiative Project.

Plasmid constructs—In order to prepare a GST-ABF fusion constructs, entire coding regions and the 3' untranslated regions of ABF1 and ABF3 were amplified by PCR using Pfu polymerase (Stratagene). After Xho I digestion followed by gel-purification, the fragments were cloned into the Sma I-Sal I sites of pGEX-5X-2 (Pharmacia Biotech). The constructs used in transactivation assay were also prepared in a similar way. The coding regions were amplified by PCR. Resulting fragments were digested with Xho I, gel-purified and cloned into pYX243. pYX243 was prepared by Nco I digestion, Klenow fill-in reaction, Sal I digestion and gel-purification. Intactness of the junction sequences was confirmed by DNA sequencing.

Preparation of recombinant ABFs and mobility shift assay—Recombinant ABF1 and ABF3 were prepared employing a GST Purification Module from Pharmacia Biotech, according to the supplier's instruction. E.coli BL21 cells were transformed with the GST-ABF constructs by electroporation. In order to prepare bacterial extract, a single colony of transformed bacteria was inoculated in 2YT/Amp medium and grown overnight. The culture was diluted (1:100) into 250 ml of fresh media. IPTG was added to the culture to a final concentration of 0.1 mM when $A_{600}$ reached 0.7. Cells were harvested by centrifugation after further growth (1.5 hr). The bacterial pellet was resuspended in 12.5 ml of PBS (0.14 M NaCl, 2.7 mM KCl, 10.1 mM $Na_2HPO_4$, 1.8 mM $KH_2PO_4$, PH7.3) and sonicated on a Branson Sonifier 250 (4×40 s burst at setting 5 at 80% duty cycle). The lysate was cleared of cell debris by centrifugation, and the supernatant was loaded onto a column packed with 0.125 ml (bed volume) of glutathione Sepharose 4B resin. Wash and elution was performed as suggested by the supplier. Protein concentration was determined using the BIO-RAD protein assay kit. Production of GST-ABF1 fusion protein was confirmed by Western blotting using GST antibody.

Mobility shift assay was performed as described (Kim et al., 1997). To prepare probes, oligonucleotide sets shown in FIG. 4 were annealed by boiling 100 pmoles each of complementary oligonucleotides for 5 min and slowly cooling to room temperature. Portions of the annealed oligonucletides (4 pmoles of each set) were labeled by Klenow fill-in reaction in the presence of $^{32}$P-dATP. Binding reactions were on ice for 30 min, and electrophoresis was performed at 4° C.

Binding site selection assay—A pool of 58 bases oligonucleotide, R58, containing 18 bases of random sequence was synthesized: CAGTTGAGCGGATCCTGTCG(N)$_{18}$GAGCGAATTCAGTGCAACT (SEQ ID NO: 19). The random sequence is flanked by Bam HI and Eco RI sites for the convenience of cloning after selection. R58 was made double strand by annealing a primer, RANR SEQ ID NO: 20), AGTTGCACTGAATTCGCCTC, and then by extending it using Klenow fragment. For the first round of selection, 5 pmoles of the double strand R58 (P0 probe) was mixed with 5 μg of the recombinant ABF1 in a 100 μl of binding buffer (10% glycerol, 25 mM HEPES, pH 7.6, 100 mM NaCl, 0.5 mM EDTA, 1 mM DTT) containing 4 μg of poly [d(I-C)] and incubated on ice for 30 min. The mixture was loaded onto 0.1 ml of glutathione Sepharose 4B resin packed on a disposable column, washed with 10 volumes of the binding buffer, and eluted with 0.3 ml of 10 mM glutathione. Bound DNA was purified by phenol/chloroform extraction followed by ethanol precipitation. Amplification of the selected DNA was performed by PCR, using 20 pmoles each of RANF (SEQ ID NO: 21) (CAGTTGAGC GGATCCTGTCG) and RANR primers in a buffer (10 mM Tris, pH 9.0, 50 mM KCl, 0.1% Triton X-100, 2.5 mM $MgCl_2$) containing 150 μM dNTP-dATP, 4 μM dATP, 10 μCi of $^{32}$P-dATP. Reaction was carried out 20 cycles (10 sec, 94° C./10 sec, 50° C./1 min, 72° C.). Amplified DNA was purified on a polyacrylamide gel, the band was excised after autoradiography, and DNA was eluted by standard method to be used as a probe DNA for the next round of selection. The selection cycle was repeated two more times. For the fourth and the fifth rounds of selection, bound DNAs were isolated after EMSA, by eluting DNA from the dried gel fragment containing the shifted bands. The amplified DNA (P5 probe) from the last selection was cloned into pBluescript (Stratagene) after Eco RI and Bam HI digestion, and plasmid DNAs from 50 random colonies were sequenced.

Transactivation assay—Reporter yeast containing the lacZ reporter gene (pYC7-I) with or without the ABRE was transformed with various pYX243/ABF constructs, and transformants were kept on Glu/CM-LEU-URA plates. For the assay, 5 colonies from each transformant group were grown in a Glu/CM-LEU-URA medium overnight to $A_{600}$ of approximately 1. The cultures were diluted 4–6 times with fresh media, grown further for 3 hr, and pelleted by brief centrifugation. The cells were washed twice with Gal/Raf/CM-LEU-URA medium, resuspended in 4 ml of the same medium, and grown for 4 hr to induce the expression of ABFs. $A_{600}$ was measured at the end of the growth period, and 0.5 ml aliquots of the culture, in duplicates, were pelleted. The pellets were resuspended in 0.665 ml of H buffer (100 mM HEPES, 150 mM NaCl, 2 mM $MgCl_2$, 1% BSA, pH 7.0) and permeabilized by vortexing for 1 min after the addition of 0.055 ml each of $CHCl_3$ and 0.1% SDS. The reaction was started by adding 0.125 ml of 40 mM stock solution of CPRG (chlorophenylred-b-D-galactopyranoside) and incubation was continued at 30° C. until the color changed to red. Reactions were stopped by the addition of 0.4 ml of 1 M $Na_2CO_3$. The mixtures were microfuged for 5 min to remove cell debris and $A_{574}$ was measured. β-galactosidase activity was expressed in Miller units.

Results

Isolation of ABRE-binding protein factors—We employed a modified yeast one-hybrid system (Kim and Thomas, 1998; Kim et al., 1997) in order to isolate ABRE-binding factor(s) using the prototypical ABRE, Emla element SEQ ID NO: 9; GGACACACGTGGCG). A cDNA expression library representing $2 \times 10^7$ cfu was constructed in a yeast expression vector pYESTrp2, using a mixture of equal amounts of mRNAs isolated from ABA- and salt-treated Arabidopsis plants. The vector contains B42 activation domain (Ma and Ptashne, 1987) whose expression is under the control of yeast GAL1 promoter. Thus, expression of cDNAs, which are inserted as a fusion to the activation domain, is inducible by galactose and repressed by glucose. The library DNA was used to transform a reporter yeast that harbors the ABRE-containing HIS3 and lacZ reporters. From a screen of 4 million yeast transformants, ca. 40 His$^+$ blue colonies were obtained, among which 19 isolates were characterized further. Analysis of the cDNA inserts of the positive clones indicated that they could be divided into 4 different groups according to their restriction patterns. Representative clones with longer inserts from each group were analyzed in more detail.

First, binding of the cDNA clones to the G/ABRE in yeast was confirmed. The G/ABRE-HIS3 reporter yeast was re-transformed with the library plasmid DNAs isolated from the representative clones. Growth pattern of the transformants on media lacking histidine was then examined to measure the HIS3 reporter activity. The result in FIG. 1 showed that transformants obtained with all four clones could grow on a galactose medium lacking histidine, but not on a glucose medium. In the same assay, the transformed yeast containing a control reporter construct lacking the ABRE could not grow on the same galactose medium. Thus, the clones could activate HIS3 reporter gene reproducibly, indicating that they bind to the ABRE in yeast.

Next, nucleotide and deduced amino acid sequences of the representative clones were determined. Clone 1, which represents two isolates, contained a cDNA insert of 1578 bp including a poly A(+) tail (FIG. 2A, SEQ ID NO. 1). An open reading frame (ORF) that is in frame with the B42 domain was present within the sequence. The ORF, referred to as ABF1 (ABRE-Binding Factor 1), contains an ATG initiation codon near the B42-cDNA junction, suggesting that it is a full-length clone. The amino acid sequence starting from the initiation codon is shown in FIG. 2A (SEQ ID NO. 2). The insert of clone 2, which represents 8 isolates, is 1654 bp long (FIG. 2B, SEQ ID NO. 3) and the longest ORF including an initiation codon near the B42-cDNA junction encodes a protein of 416 amino acids (ABF2) (FIG. 2B, SEQ ID NO. 4).

The insert of clone 11, representing 6 isolates, encoded a protein containing 434 amino acids. An ORF containing 366 amino acids was found in clone 19 cDNA. The clones were partial, however, and the missing 5' portions were isolated using the available partial sequence information on databases (Materials and methods). Sequencing of the full-length clones (FIGS. 2C and 2D, SEQ ID NOs. 5 and 7) showed that the original clone 11 was missing the first 20 amino acids, and thus, full-length clone 11 encodes a protein containing 454 amino acids (ABF3) (FIG. 2C, SEQ ID NO. 6). The longest ORF of clone 19 is composed of 431 amino acids (ABF4) (FIG. 2D, SEQ ID NO. 8).

ABFs are bZIP proteins—Analysis of the deduced amino acid sequence of ABF1 revealed that it has a basic region near its C-terminus (SEQ ID NO: 2; FIGS. 2A and 3). The region immediately downstream of it contains 4 heptad repeats of leucine, indicating that ABF1 is a bZIP protein (Landshulz et al., 1988). Similarly, other ABFs also have a basic region followed by a leucine repeat region (SEQ ID NO: 4, SEQ ID NO: 6, SEQ ID NO: 8; FIGS. 2B–D and 3). The basic regions of ABF1 and ABF3 (SEQ ID NO: 2, SEQ ID NO: 6, respectively) are identical to each other, and those of ABF 2 and (SEQ ID NO: 4, SEQ ID NO: 8, respectively) are also identical (FIG. 3). The two, shared basic regions are same except that one of the lysine residues of ABF1 and ABF3 is replaced by arginine in ABF 2 and ABF4. The analysis shows that a family of bZIP proteins with conserved basic regions interacts with the G/ABRE.

ABFs also share several highly conserved regions outside the basic domains. As shown in FIG. 3, the conserved regions are clustered in the N-terminal halves. Invariably, they contain one or two potential phosphorylation sites. The N-most region, for example, contains one multifunctional calmodulin-dependent protein kinase II (CaMK II) site (X-R-X-X-S*-X) (Kemp and Pearson, 1990) followed by a caseine kinase II (CKII) phosphorylation site (X-S/T*-X-X-D/E-X). One or two CaMK II or CK II phosphorylation sites are also present in other conserved regions. The middle portions of ABFs are highly variable and rich in glutamine commonly found in transcriptional activation domains.

Figure 4A:
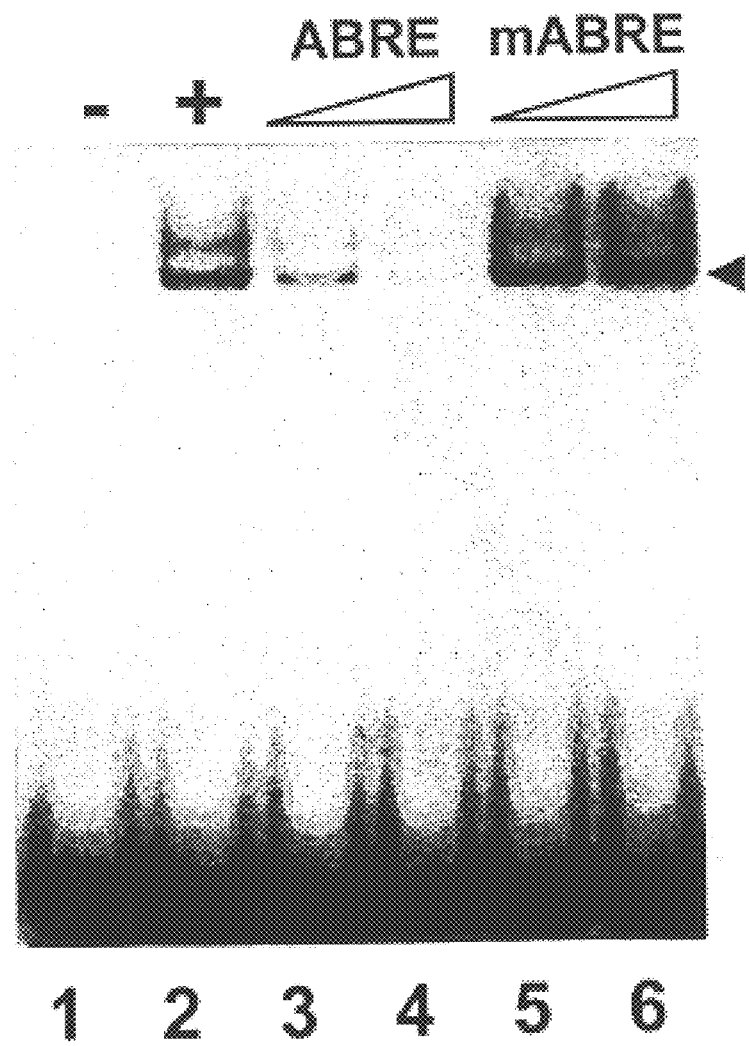
FIGS. 4A–4B. Electrophoretic mobility shift assay.

In vitro binding activity of ABFs—In order to test in vitro DNA-binding activity of ABFs, we performed electrophoretic mobility shift assay (EMSA) using recombinant ABF1 or ABF3 and probe DNAs containing a G/ or C/ABRE. Similar results were obtained with both proteins and the assay result of ABF1 is shown in FIG. 4. A major shifted band was observed, with a weaker minor band (FIG. 4A, lane 2). Addition of excess, increasing amount of unlabeled probe DNA to the reaction mixture (lanes 3 and 4) gradually abolished the binding, whereas the same amount of a mutated oligonucleotide (lanes 5 and 6) did not. Thus, ABF1 and ABF3 exhibited sequence-specific binding activity to the G/ABRE in vitro.

Figure 4B:
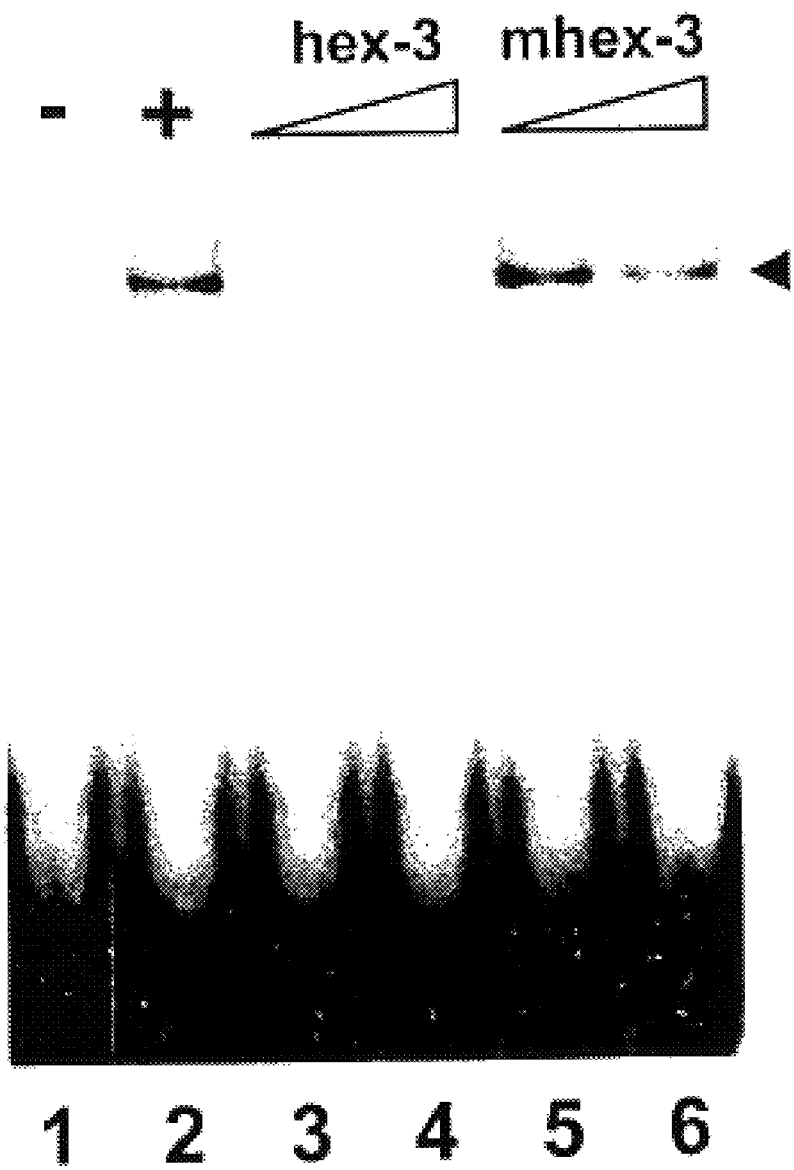

ABFs are similar to the Dc3 promoter-binding factors (DPBFs) (Kim and Thomas, 1998; Kim et al., 1997) in their basic regions (see Discussion). Since DPBFs are known to interact not only with a G/ABRE but also with C/ABREs, we tested whether ABFs can interact with C/ABREs. To date, no transcriptional activators interacting with the element were reported except the embryo-specific DPBFs. An oligonucleotide, hex-3 (SEQ ID NO: 13; LaM and Chua, 1991), containing the C/ABRE core sequence (CGCGTG), was employed as a probe in an EMSA. As shown in FIG. 4B, a shifted band was observed (lane 2). The band formation was abolished by the addition of excess amounts of the cold probe DNA to the reaction mixture (lanes 3 and 4). The competition was not observed with a mutated probe DNA (lanes 5 and 6), demonstrating that the binding was specific to the C/ABRE. Thus, ABF1 and ABF3 could bind to a C/ABRE as well.

Figure 5A:
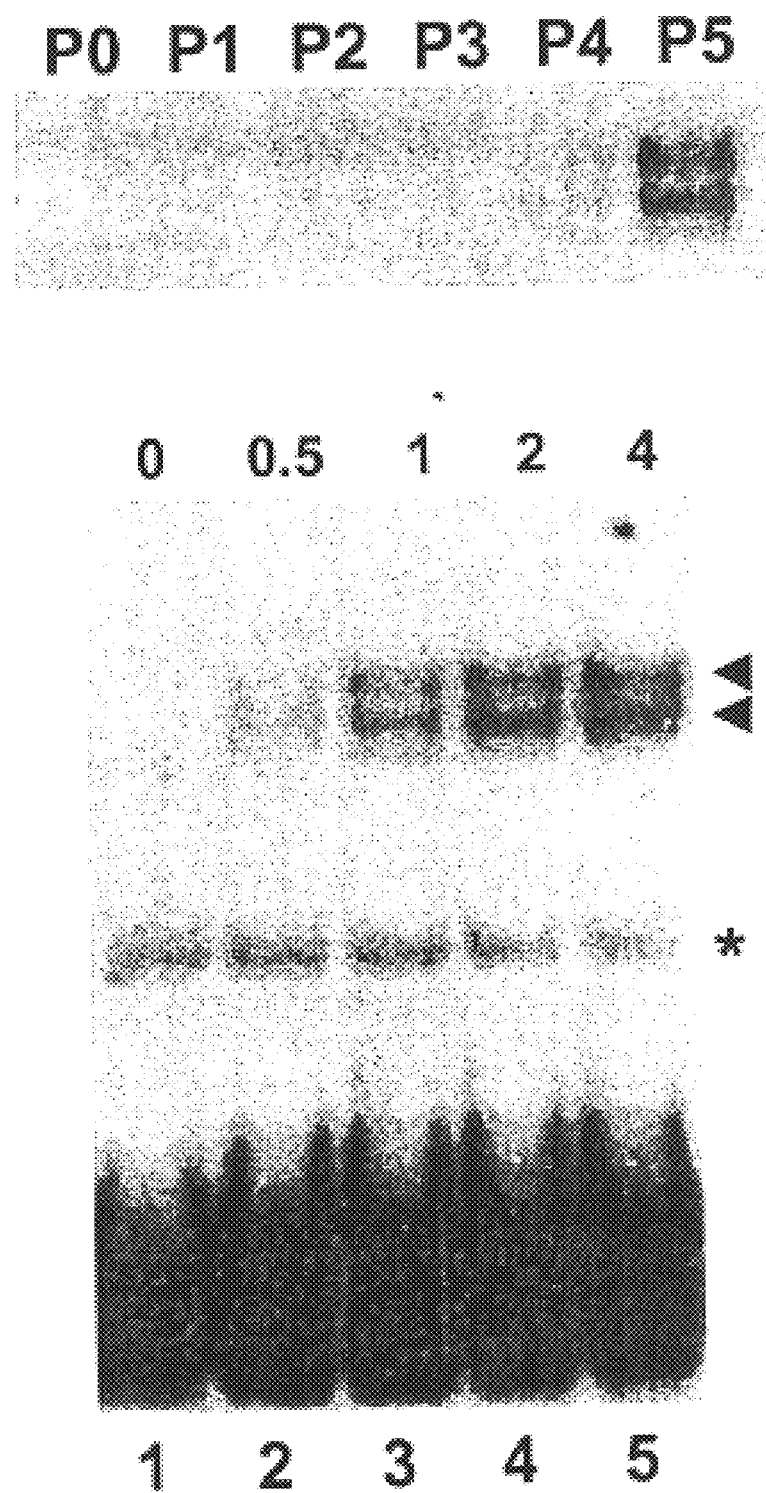

Binding site preference of ABF1—Our in vitro binding assay indicated that ABF1 and ABF3 can interact with both G/ and C/ABREs, although mutual competition assay (not shown) showed that they have higher affinity to the G/ABRE. In order to investigate ABF binding sites further, we performed a random binding site selection assay (RBSA) (Pollock and Treisman, 1990) (Materials and methods), using the recombinant ABF1. Shifted bands were visible on a mobility shift assay gel after three rounds of selection (FIG. 5A, top panel). After confirming the binding of ABF1 to the probe DNAs from the final round of selection (FIG. 5A. bottom panel), the DNAs were cloned and sequenced.

The 44 selected sequences are presented in FIG. 5B. The sequences could be divided into 4 groups (groups IA, IAA, IB, and II) according to their consensus sequences. All of the group I sequences, except one (sequence no. 49), contain an ACGT element, while the group II sequences contain the C/ABRE core. The most frequently selected sequences (30 of 44) are those sharing a strong G/ABRE, CACGTGGC (Busk and Pages, 1998): gACACGTGGC (SEQ ID NO: 22; group IA or CCACGTGGC (group IAA). The group IAA element is similar to the prototypical ABRE, Em1a (SEQ ID NO: 9; GGACACGTGGC), while the group IIA consensus is the same as the palindromic G/ABREs present in many ABA-inducible genes such as maize rab28, Arabidopsis kin1, cor6.6 and Adh1 genes (reviewed in Thomas et al., 1997). In some of the group IA sequences (sequence no. 38, 45 and 42), the GGC following the ACGT core is replaced by GTC, forming another palindromic consensus sequence, GACACGTGTC (SEQ ID NO: 23.). The group IB sequences share a GNTGACGTGGC (SEQ ID NO: 24) consensus or its variants differing in one or two bases flanking the ACGT core. Although the conserved element differs from those of group IA and IAA in the bases preceding the ACGT core, it contains the same ACGTG(G/t)C. Hence, the preferred binding sites of ABF1 can be represented as ACGTG(G/t)C, with AC, CC or TG preceding it.

One of the selected sequences (no.24 of group II) contains the C/ABRE core sequence (CGCGTG). The three other group II sequences also contain the C/ABRE core. The element in them, however, is flanked by one of the group I consensus sequences, and thus, they contain both types of ABREs. Another sequence (no. 49 of group IB) does not contains the ACGT core; the C of the ACGT is replaced by A. The resulting AAGTGGA sequence is similar to the half G-box (CCAAGTGG) of Arabidopsis Adh1 promoter, which is required for high level ABA-induction of the gene (de Bruxelles et al., 1996). Thus, ABF1 interacts with sequences without the ACGT core, which includes the C/ABRE. The low selection frequency, however, suggests that ABF1's affinity to them is lower.

Figure 6A:
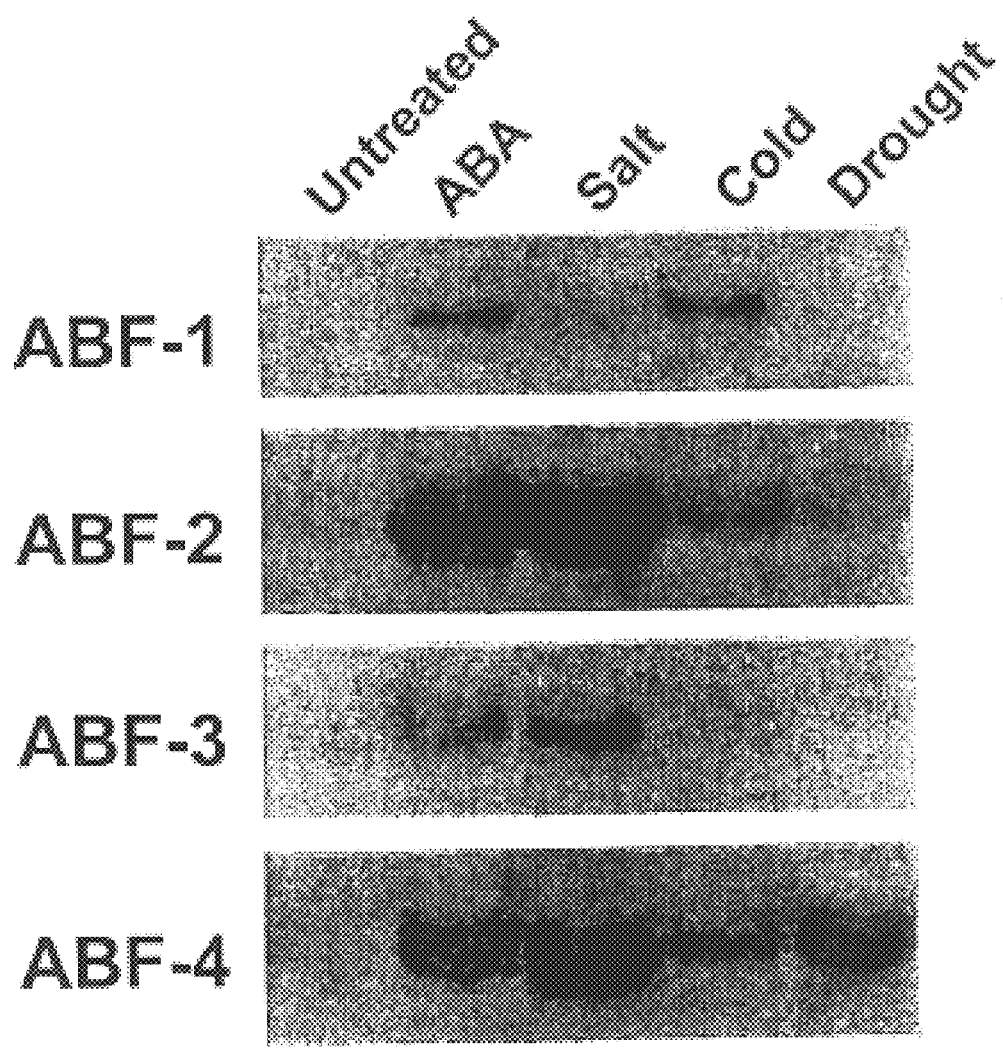
FIGS. 6A–6B. Analysis of ABF expression. ABA- and stress-inducibility of ABF expression were examined by RNA gel blot analysis or RT-PCR. A, inducibility of ABF expression. 25 μg of total RNAs isolated from untreated plants or plants treated with ABA, high salt, cold or drought, were transferred to a membrane and probed with specific probes. B, time course of ABA-induction. RT-PCR reactions were performed using 0.5 μg total RNAs from plants treated with 100 μM ABA for 0 min, 30 min, 1 hr, 2 hr, 4 hr, 8 hr 12 hr, 16 hr, and 24 hr. actin, a control reaction performed with an actin gene of *Arabidopsis thaliana*.

Expression of ABFs is ABA-inducible—Since we are interested in ABA-inducible stress responsive factors, we investigated ABA-inducibility of ABF expression, by RNA gel blot analysis (FIG. 6A). With the ABF1 probe, no hybridization signal was detectable with RNA isolated from untreated plants, while a clear signal was detected with RNA from ABA-treated plants. Similar results were obtained with other ABF probes; while hybridization signals were weak (ABF2 and 4) or undetectable (ABF-3) with the RNA from untreated plants, distinct signals were observed with the RNA sample from ABA-treated plants. Thus, expression of ABFs is ABA-inducible.

Figure 6B:
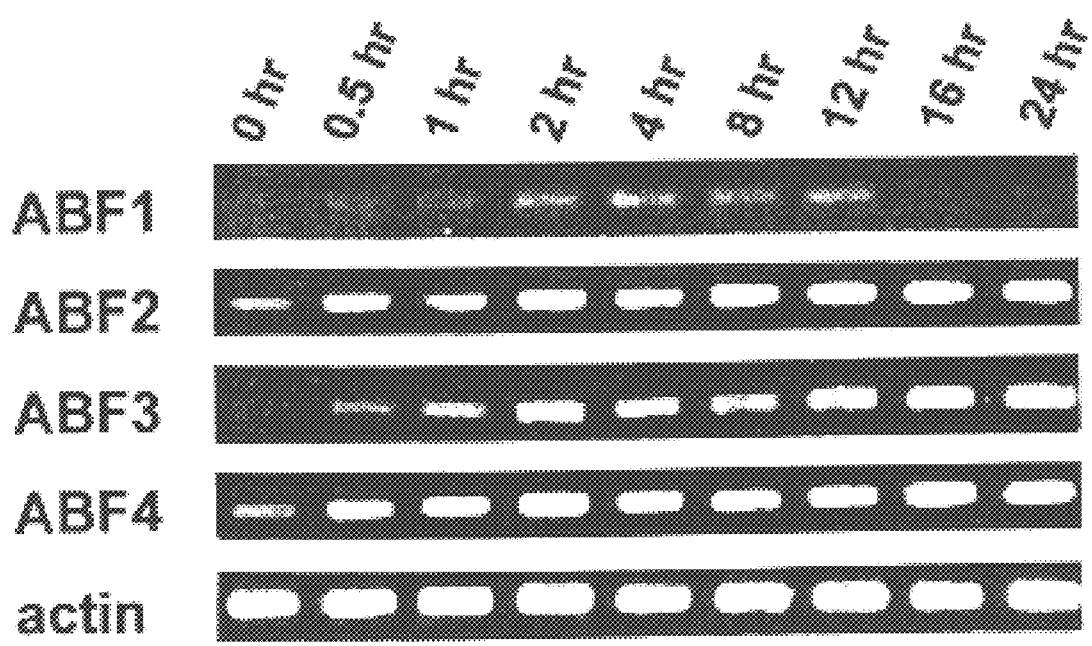

Although all are induced by ABA, the time course of ABA-induced expression of ABFs was not identical to each other (FIG. 6B). ABF1 RNA level reached a peak approximately 2 hours after ABA treatment started, remained same up to 12 hours and decreased to the uninduced level after 16 hours. ABF2 and ABF4 expression appeared to be induced faster, reaching a plateau after 30 min of ABA treatment. Afterwards, their RNA level remained relatively same until 24 hour. The induction pattern of ABF3 was similar to those of ABF2 and ABF4 except that it reached the peak level later, i.e., after 2 hours.

We also examined the effect of various environmental stresses on the expression of ABFs. The results (FIG. 6A) showed that expression of ABF1 was induced by cold treatment, but not by other stress treatments. With the same RNA samples, ABF2 and ABF3, on the other hand, were not induced by cold, but by high salt treatment. ABF4 expression was induced by all three treatments, although induction level after cold treatment was relatively low. Expression of ABFs is, thus, inducible also by various environmental stresses and their induction patterns are differential, suggesting that they function in different stress responsive pathways.

ABFs can transactivate an ABRE-containing reporter gene in yeast—Our result so far demonstrated that ABF1, and probably other ABFs too, can bind to various ABREs and that their expression is both ABA- and stress-dependent. Thus, ABFs have potential to activate a large number of ABA/stress responsive genes, if they have transactivation capability. We therefore investigated whether ABFs can activate an ABRE-containing reporter gene. Coding regions of ABFs were cloned into a yeast expression vector and the constructs were individually introduced into a yeast strain that harbored a G/ABRE-containing lacZ reporter gene integrated into the chromosome. Subsequently, reporter enzyme activity was measured.

With the ABF1 construct, β-galactosidase activity was 6 times higher than that obtained with the control construct (FIG. 7, top panel). No enzyme activity was detectable with the same ABF1 construct when a reporter lacking the ABRE was used. Thus, ABF1 can transactivate the reporter gene and the activation is ABRE-dependent. With the ABF2 construct, reporter enzyme activity two times higher than the background activity was detected, indicating that the factor also can transactivate the reporter gene (FIG. 7, top panel). Likewise, ABF3 and 4 could transactivate the reporter gene (FIG. 7, bottom panel). The activation level of ABF3 was higher than the ABF1's, while ABF4 showed weaker activation. The result of our transactivation assay demonstrates that ABFs can activate an ABRE-containing gene in yeast.

Discussion Numerous studies, both genetic and biochemical, show that ABA mediates stress response in vegetative tissues, although not all stress responses are ABA-dependent (Leung and Giraudat, 1998; Shinozaki and Yamaguchi-Shinozaki, 1996; Thomashow, 1998; Ingram and Bartels, 1996). Central to the response is the ABA-regulation of gene expression through G/ABREs or C/ABREs. Transcription factors mediating ABA-independent cold and drought responses have been reported recently (Jaglo-Ottosen et al., 1998; Liu et al., 1998). However, those regulating ABA-dependent stress response via the G/ or the C/ ABREs have yet to be identified. Among the ABRE-binding factors mentioned earlier, TAF-1 is known not to be directly involved in ABA responsive gene expression (Oeda et al., 1991), while EmBP-1 and DPBFs are highly embryo-specific (Kim and Thomas, 1998; Hollung et al., 1997). GBF3 and a homology-based cloned factor OSBZ8, although inducible by ABA, are from cultured cells or from embryos (Lu et al., 1996; Nakagawa et al., 1996). Taken together with the lack of data demonstrating their role in ABA or stress response, it is likely that unknown factors may mediate ABA-responsive gene expression in vegetative tissues.

Figure 8B:
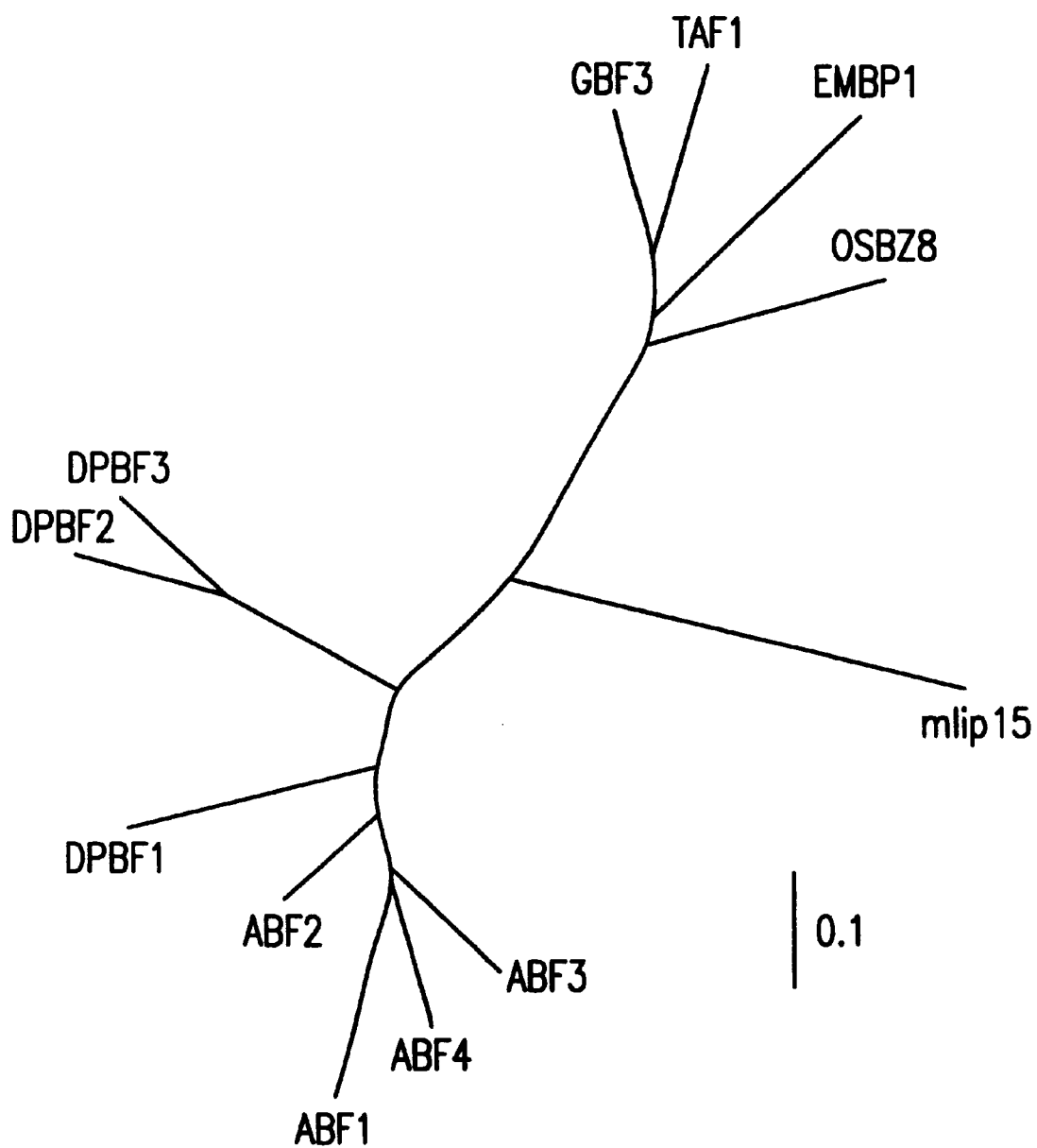

In a search for such transcription factors, we isolated a family of G/ABRE-binding proteins from young Arabidopsis plants treated with ABA or high salt. The factors, referred to as ABFs, are ABA/stress-inducible bZIP class transcription factors with shared basic regions. Sequence comparison with known ABRE-binding factors indicated that, although they do not show any significant homology to other factors, they are similar to the Dc3 promoter-binding factors (DPBFs) (Kim and Thomas, 1998; Kim et al., 1997). DPBFs have been isolated from a seed-specific library based on their interaction with a lea gene promoter containing both G/ and C/ABREs. The two family members are nearly identical in their basic regions (FIG. 8A), and their DNA-binding properties are similar in that they can interact with both types of ABREs. Some of the conserved phosphorylation sites within the N-terminal halves of ABFs are also conserved in DPBFs. However, ABFs diverge from the DPBFs outside the basic regions and their immediate flanking sequences, overall identity being in the range of 30–40%. As a result, they form a subfamily distinct from DPBFs and also from other known factors, as shown in FIG. 8B. Furthermore, their expression patterns are different from those of DPBFs; i.e., DPBFs' expression is embryo-specific. Cloning of ABFs shows that two related subfamilies of ABRE-binding factors are present in seed and in vegetative tissues, respectively. The presence of distinct factors in the tissues that have similar ABRE-binding affinity has been demonstrated in maize (Pla et al., 1993).

ABFs contain regions highly conserved among them apart from the basic regions. Thus, ABFs appear to share some properties other than DNA-binding activity. The conserved regions, however, do not have any easily recognizable motifs except that two of them can form α-helix, and thus, their function remains to be identified. They may be involved in nuclear translocation, DNA-binding, transcriptional activation, or interaction with other regulatory proteins. Whatever their function may be, the conservation of potential phosphorylation sites within the regions suggests that it is probably modulated by post-translational modification.

Our in vitro binding assay showed that the most preferred binding site of ABF1 in vitro can be represented as CACGTGGC (FIG. 5B). The element, first identified as EmBP-1 recognition site (Guiltinan et al., 1990), are highly conserved among ABA/stress inducible promoters and strongly affect ABA-inducibility in vivo (Busk and Pages, 1998). Together with the fact that ABF1 is ABA/stress-inducible and has transcriptional activity, this suggests that ABF1 can potentially activate a large number of ABA/stress responsive genes. Also, ABF1 can bind to other ABREs including the C/ABREs, further supporting the broad spectrum of potential ABF1 target genes. The affinity to C/ABREs, however, was relatively low in vitro.

The expression pattern of ABFs suggests that each ABF is likely to be involved in different stress signaling pathways. Although all are ABA-inducible and can bind to same ABREs, they are differentially regulated by various environmental stresses. ABF1 expression is induced by cold, ABF 2 and ABF3 by high salt, and ABF4 by cold, high salt and drought. The simplest interpretation of the result would be that ABF1 is involved in cold signal transduction, while ABF2 and ABF3 function in osmotic stress signaling. ABF4, on the other hand, appears to participate in multiple stress responses. In addition, ABFs differ in their ABA induction patterns. Expression of ABF1 was induced rather slowly (FIG. 6B) and the accumulation of its RNA was transient, while induction of other ABFs appeared faster and their RNA levels remained relatively stable once reached a plateau. The multiplicity of ABA-dependent stress signaling pathways has been demonstrated in Arabidopsis by genetic analysis (Leung and Giraudat, 1998; Ishitani et al., 1997). Our result suggests further that multiple transcription factors are likely to function in these signal transduction cascades through common ABREs.

ABA-dependent stress responsive gene expression is critical to plant growth and productivity. Here, we reported a family of transcription factors that interact with cis-regulatory elements mediating this process. Although their specific roles in planta remains to be determined, our data presented here suggest that they are likely to be involved in various ABA-mediated stress responses. They can bind to ABREs highly conserved among stress responsive promoters. They can transactivate an ABRE-containing reporter gene. Their expression is induced by ABA and by various environmental stresses. Hence, ABFs are excellent targets of genetic manipulation for the generation of stress tolerant transgenic plants.

REFERENCES

Altschul, S. F., Gish, W., Miller, W., Myers, E. W. and Lipman, D. J. (1990). Basic local alignment search tool. *J. Mol. Biol.* 215, 403–410.

Ausubel, F. M., Brent, R., Kingston, R. E., Moore, D. D., Seidman, J. G., Smith, J. A. and Struhl, K. (1994). *Current Protocols in Molecular Biology* (New York: Green Publishing Associates/Wiley Interscience).

de Bruxelles G. L., Peacock, W. J., Dennis, E. S. and Dolferus, R. (1996). Abscisic acid induces the alcoholdehydrogenase gene in Arabidopsis. *Plant Physiol.* 111, 381–391.

Busk, P. K., Jensen, A. B. and Pages, M. (1997). Regulatory elements in vivo in the promoter of the abscisic acid responsive gene rab17 from maize. *Plant J.* 11, 1285–1295.

Busk, P. K. and Pages, M. (1998). Regulation of abscisic acid-induced transcription. *Plant Mol. Biol.* 37, 425–435.

Chomczynski, P. and Mackey, K. (1995). Modification of the TRI reagent procedure for isolation of RNA from polysaccharide- and proteoglycan-rich sources. *BioTechniques* 19, 942–945.

Foster, R., Izawa, T. and Chua, N.-H. (1994). Plant bZIP proteins gather at ACGT elements. *FASEB J.* 8, 192–199.

Guiltinan. M. J., Marcotte, W. R. and Quatrano, R. S. (1990). A plant leucine zipper protein that recognizes an abscisic acid responsive element. *Science* 250, 267–271.

Guthrie, C. and Fink, G. R. eds. (1991). Guide to Yeast Genetics and Molecular Biology. *Methods Enzymol* 194.

Hollung, K., Espelund, M., Schou, K., and Jakobsen, K. S. (1997) *Plant Mol. Biol.* 35, 561–571.

Ingram, J. and Bartels, D. (1996). The molecular basis of dehydration tolerance in plants. *Ann. Rev. Plant Physiol. Plant Mol. Biol.* 47, 377–403.

Ishitani, M., Xiong, L., Stevenson, B. and Zhu, J.-K. (1997). Genetic analysis of osmotic and cold stress signal transduction in Arabidopsis: interactions and convergence of abscisic acid-dependent and abscisic acid-independent pathways. *Plant Cell* 9, 1935–1949.

Jaglo-Ottosen, K. R., Gilmour S. J., Zarka, D. G., Schabenberger and Thomashow, M. F. (1998). Arabidopsis CBF1 overexpression induces COR genes and enhances freezing tolerance. *Science* 280, 104–106.

Kasuga, M., Liu, Q., Miura, S., Yamaguchi-Shinozaki, K. and Shinozaki, K. (1999). Improving plant drought, salt, and freezing tolerance by gene transfer of a single stress-inducible transcription factor. *Nature Biotech.* 17, 287–291.

Kemp, B. E. and Pearson, R. B. (1990). Protein kinase recognition sequence motifs. *Trends Biochem. Sci.* 15, 342–346.

Kim, S. Y. and Thomas, T. L. (1998). A family of basic leucine zipper proteins bind to seed-specification elements in the carrot Dc3 gene promoter. *J. Plant Physiol.* 152, 607–613.

Kim, S. Y., Chung, H.-J. and Thomas, T. L. (1997). Isolation of a novel class of bZIP transcription factors that interact with ABA-responsive and embryo-specification elements in the Dc3 promoter using a modified yeast one-hybrid system. *Plant J.* 11, 1237–1251.

Kusano, T., Berberich, T., Harada, M., Suzuki, N. and Sugawara, K. (1995). A maize DNA-binding factor with a bZIP motif is induced by low temperature. *Mol. Gen. Gent.* 248, 507–517.

Lam, E. and Chua, N.-H. (1991). Tetramer of a 21-base pair synthetic element confers seed expression and transcriptional enhancement in response to water stress and abscisic acid. *J. Biol. Chem.* 266, 17131–17135.

Landschulz, W. H., Johnson, P. F. and McKnight, S. L. (1988). The leucine zipper: A hypothetical structure common to a new class of DNA binding proteins. *Science* 240, 1759–1764.

Leung, J. and Giraudat, J. (1998). Abscisic acid signal transduction. *Ann. Rev. Plant physiol. Plant Mol. Biol.* 49, 199–222.

Liu, Q, Kasuga, M., Sakuma, Y., Abe, H., Miura, S., Yamaguchi-Shinozaki, K. and Shinozaki, K. (1998). Two transcription factors, DREB1 and DREB2, with an EREBP/AP2 DNA binding domain separate two cellular signal transduction pathways in drought- and low temperature-responsive gene expression, respectively, in Arabidopsis. *Plant Cell* 10, 1391–1406.

Lu, G., Paul, A.-L., McCarty D. R. and Ferl, R. J. (1996). Transcription factor veracity: Is GBF3 responsible for ABA-regulated expression of Arabidopsis Adh? *Plant Cell* 8, 847–857.

Ma, J. and Ptashne, M. (1987). A new class of yeast transcriptional activators. *Cell* 51, 113–119.

Menkens, A. E., Schindler U. and Cashmore, A. R. (1995). The G-box: a ubiquitous regulatory DNA element in plants bound by the GBF family of bZIP proteins. *Trend Biochem Sci.* 20, 506–510.

Nakagawa, H., Ohmiya, K. and Hattori, T. (1996). A rice bZIP protein, designated as OSBZ8, is rapidly induced by abscisic acid. *Plant J.* 9, 217–227.

Oeda, K., Salinas, J. and Chua, N.-H. (1991). A tobacco bZIP transcription activator (TAF-1) binds to a G-box-like motif conserved in plant genes. *EMBO J.* 10, 1793–1802.

Ono, A., Izawa, T., Chua, N.-H. and Shimamoto, K. (1996). The rice rab16B promoter of rice contains two distinct abscisic acid-responsive elements. *Plant physiol.* 112, 483–491.

Pla, M., Vilardell, J., Guiltinan, M. J., Marcotte, W. R., Niogret, M. F., Quatrano, R. S. and Pages, M. (1993). The cis-regulatory element CCACGTGG is involved in ABA and water-stress response of the maize gene rab28. *Plant Mol. Biol.* 21, 259–266.

Pollock, R. and Treisman. R. (1990). A sensitive method for the determination of protein-DNA binding specificities. *Nucl Acids Res.* 18, 6197–6204.

Sambrook, J., Fritsch, E. F. and Maniatis, T. (1989). *Molecular Cloning: A laboratory Manual*, $2^{nd}$ ed. (Cold Spring Harbor, N.Y.: Cold Spring Harbor Laboratory Press).

Schindler, U., Menkens, A. E., Beckmann, H., Ecker, J. R. and Cashmore, A. R. (1992). Heterodimerization between light-regulated and ubiquitously expressed Arabidopsis GBF bZIP proteins. *EMBO J.* 4, 1261–1273.

Shinozaki, K. and Yamaguchi-Shinozaki, K. (1996). Molecular responses to drought and cold stress. *Curr. Opin. Biotech.* 7, 161–167.

Thomas, T. L., Chung, H.-J. and Nunberg, A. N. (1997). ABA signaling in plant development and growth. In *Signal Transduction in Plants*, (Aducci, P. ed.). Basel: Birkhauser Verlag, pp. 23–43.

Thomashow, M. F. (1998). Role of cold-responsive genes in plant freezing tolerance. *Plant Physiol.* 118, 1–7.

Thompson, J. D., Higgins, D. G. and Gibson, T. J. (1994). CLUSTAL W: improving the sensitivity of progressive multiple sequence alignment through sequence weighting, position-specific gap penalties and weight matrix choice. *Nucleic Acids Res.* 22, 4673–4680.

Yamaguchi-Shinozaki, K., and Shinozaki, K. (1994). A novel cis-acting element in an Arabidopsis gene is involved responsiveness to drought, low-temperature, or high-salt stress. *Plant Cell* 6, 251–264.

What is claimed is:

1. An isolated nucleic acid molecule encoding the Abscisic acid responsive element-binding factor 4 (ABF4) having the amino acid sequence of SEQ ID NO:8.

2. The isolated nucleic acid molecule of claim 1, wherein the nucleic acid molecule is a messenger RNA molecule.

3. The isolated nucleic acid molecule of claim 1, wherein the nucleic acid molecule is a cDNA having the nucleotide sequence of SEQ ID NO:7.

* * * * *

UNITED STATES PATENT AND TRADEMARK OFFICE
CERTIFICATE OF CORRECTION

PATENT NO.   : 6,232,461 B1                                    Page 1 of 1
DATED        : May 15, 2001
INVENTOR(S)  : Soo Young Kim It is certified that error appears in the above-identified patent and that said Letters Patent is hereby corrected as shown below:

<u>Title page,</u>
Line 5, change "RACTOR 4" to -- FACTOR 4 --.

<u>Column 1,</u>
Line 3, change "RACTOR 4" to -- FACTOR 4 --.

Signed and Sealed this

Eighth Day of January, 2002

Attest:

Attesting Officer

JAMES E. ROGAN
*Director of the United States Patent and Trademark Office*

SEQUENCE LISTING

<160> NUMBER OF SEQ ID NOS: 83

<210> SEQ ID NO: 1
<211> LENGTH: 1578
<212> TYPE: DNA
<213> ORGANISM: Arabidopsis thaliana

<400> SEQUENCE: 1

| | | | | | |
|---|---|---|---|---|---|
| aaagggtctg | attcgtttgt | tttttcactg | aagaatttgg | aaggaagtga | ttccgttgtg | 60 |
| aaacagaaaa | gaagtatggg | tactcacatt | gatatcaaca | acttaggcgg | cgatacttct | 120 |
| agagggaatg | agtcaaagcc | attggcgagg | cagtcttcgt | tatattcctt | aacgtttgat | 180 |
| gagcttcaga | gcacattagg | tgagccgggg | aaagattttg | ggtctatgaa | tatggatgag | 240 |
| ttactcaaga | acatatggac | tgctgaggat | actcaagcct | ttatgactac | tacatcttcg | 300 |
| gttgcagccc | cgggacctag | tggttttgtt | ccgggaggaa | atggtttaca | gaggcaaggc | 360 |
| tccttgacct | tgcctagaac | gcttagtcag | aagactgtcg | atgaagtctg | gaaatacctg | 420 |
| aattcgaaag | aaggtagtaa | tgggaatact | ggaacggatg | cgcttgagag | gcaacagact | 480 |
| ttaggggaaa | tgactctgga | agatttctta | ctccgtgctg | gcgttgttaa | agaagataat | 540 |
| actcagcaga | acgaaaacag | tagtagcggg | ttttatgcta | caacggtgc | tgctggtttg | 600 |
| gagtttggat | ttggtcagcc | gaatcaaaac | agcatatcgt | tcaacgggaa | caatagttct | 660 |
| atgatcatga | atcaagcacc | tggtttaggc | ctcaaagttg | gtggaaccat | gcagcagcag | 720 |
| cagcagccac | atcagcagca | gttgcagcag | ccacatcaga | gactgcctcc | aactatcttt | 780 |
| ccaaaacaag | cgaatgtaac | atttgcggcg | cctgtaaata | tggtcaacag | gggtttattt | 840 |
| gagactagcg | cagatggtcc | agccaacagt | aatatgggag | gagcaggggg | tactgttaca | 900 |
| gctacttctc | ctgggacgag | cagtgcagaa | acaatactt | ggtcatcacc | agttccttac | 960 |
| gtgtttggtc | ggggaagaag | aagcaatacg | ggcctggaga | aggttgttga | gagaaggcaa | 1020 |
| aagagaatga | tcaagaatcg | ggaatccgct | gctagatcaa | gggctcgaaa | acaggcttat | 1080 |
| accttggaac | tggaagctga | gattgaaagt | ctcaagctag | tgaatcaaga | tttgcagaag | 1140 |
| aaacaggctg | aaataatgaa | acccataat | agtgagctaa | aggaattttc | gaagcagcct | 1200 |
| ccattgctgg | ccaaaagaca | atgcttgaga | agaacccta | ccggtccgtg | gtaagaaggt | 1260 |
| gaagtcaaag | caagaagaac | ctgctaatgt | aatacaggac | cactcaaaag | gaagacactg | 1320 |
| ggagagtaat | atgtaataga | agatagtgct | actgtacagg | agaaattaca | gagacgctta | 1380 |
| caatgtagaa | atcttttgag | ctgaatttaa | ctaagagtgc | agtctgtgta | gagtatgaga | 1440 |
| gctttcaata | tgaattcata | attttcataa | acatatgtaa | aactttcaga | tttagctata | 1500 |
| gagaagatgt | gactaaaaaa | aaaaaaaaaa | aaaaaaaaaa | aaaaaaaaaa | aaaaaaaaaa | 1560 |
| aaaaaaaaaa | aaaaaaaa | | | | | 1578 |

<210> SEQ ID NO: 2
<211> LENGTH: 392
<212> TYPE: PRT
<213> ORGANISM: Arabidopsis thaliana

<400> SEQUENCE: 2

Met Gly Thr His Ile Asp Ile Asn Asn Leu Gly Gly Asp Thr Ser Arg
 1               5                  10                  15

Gly Asn Glu Ser Lys Pro Leu Ala Arg Gln Ser Ser Leu Tyr Ser Leu
             20                  25                  30

```
Thr Phe Asp Glu Leu Gln Ser Thr Leu Gly Glu Pro Gly Lys Asp Phe
         35                  40                  45
Gly Ser Met Asn Met Asp Glu Leu Leu Lys Asn Ile Trp Thr Ala Glu
 50                  55                  60
Asp Thr Gln Ala Phe Met Thr Thr Ser Ser Val Ala Ala Pro Gly
 65                  70                  75                  80
Pro Ser Gly Phe Val Pro Gly Gly Asn Gly Leu Gln Arg Gln Gly Ser
             85                  90                  95
Leu Thr Leu Pro Arg Thr Leu Ser Gln Lys Thr Val Asp Glu Val Trp
            100                 105                 110
Lys Tyr Leu Asn Ser Lys Glu Gly Ser Asn Gly Asn Thr Gly Thr Asp
            115                 120                 125
Ala Leu Glu Arg Gln Gln Thr Leu Gly Glu Met Thr Leu Glu Asp Phe
130                 135                 140
Leu Leu Arg Ala Gly Val Val Lys Glu Asp Asn Thr Gln Gln Asn Glu
145                 150                 155                 160
Asn Ser Ser Ser Gly Phe Tyr Ala Asn Asn Gly Ala Ala Gly Leu Glu
                165                 170                 175
Phe Gly Phe Gly Gln Pro Asn Gln Asn Ser Ile Ser Phe Asn Gly Asn
            180                 185                 190
Asn Ser Ser Met Ile Met Asn Gln Ala Pro Gly Leu Gly Leu Lys Val
            195                 200                 205
Gly Gly Thr Met Gln Gln Gln Gln Gln Pro His Gln Gln Leu Gln
        210                 215                 220
Gln Pro His Gln Arg Leu Pro Pro Thr Ile Phe Pro Lys Gln Ala Asn
225                 230                 235                 240
Val Thr Phe Ala Ala Pro Val Asn Met Val Asn Arg Gly Leu Phe Glu
                245                 250                 255
Thr Ser Ala Asp Gly Pro Ala Asn Ser Asn Met Gly Gly Ala Gly Gly
            260                 265                 270
Thr Val Thr Ala Thr Ser Pro Gly Thr Ser Ser Ala Glu Asn Asn Thr
            275                 280                 285
Trp Ser Ser Pro Val Pro Tyr Val Phe Gly Arg Gly Arg Arg Ser Asn
290                 295                 300
Thr Gly Leu Glu Lys Val Val Glu Arg Arg Gln Lys Arg Met Ile Lys
305                 310                 315                 320
Asn Arg Glu Ser Ala Ala Arg Ser Arg Ala Arg Lys Gln Ala Tyr Thr
                325                 330                 335
Leu Glu Leu Glu Ala Glu Ile Glu Ser Leu Lys Leu Val Asn Gln Asp
            340                 345                 350
Leu Gln Lys Lys Gln Ala Glu Ile Met Lys Thr His Asn Ser Glu Leu
            355                 360                 365
Lys Glu Phe Ser Lys Gln Pro Pro Leu Leu Ala Lys Arg Gln Cys Leu
            370                 375                 380
Arg Arg Thr Leu Thr Gly Pro Trp
385                 390
```

<210> SEQ ID NO: 3
<211> LENGTH: 1654
<212> TYPE: DNA
<213> ORGANISM: Arabidopsis thaliana

<400> SEQUENCE: 3
cccaaacgaa gaaccaaaca ttttgaaatt ttttgggaaa attacaaagc acacgaattt    60

-continued

```
agcaaaaaga tccagttatt aggtggaagc agattttgta gaaaaatgga tggtagtatg      120
aatttgggga tgagccacc aggagatggt ggtggaggtg gagggttgac tagacaaggt       180
tcgatatact cgttgacgtt tgatgagttt cagagcagtg tagggaaaga ttttgggtca      240
atgaacatgg atgagttgtt aaagaatata tggagtgctg aagaaacaca agccatggct      300
agtggtgtgg ttccagttct tggtggaggt caagagggtt tgcagctgca gaggcaaggc      360
tcgttgactc tgcctcgaac gcttagtcag aagacggttg atcaagtttg aaagatcta       420
tccaaagttg aagtagtgg agtaggggga gtaacttgt ctcaggtggc tcaggctcag        480
agtcagagtc agagtcagag gcagcaaaca ttaggtgaag taactttgga ggagttttg      540
gttcgtgctg tgttgtgag agaggaagct caggttgctg caagagctca gattgctgag      600
aacaataaag gcggttactt tggtaatgat gccaacacag gtttctctgt cgagtttcag      660
cagccttctc cacgagttgt tgccgctggt gtaatgggaa atcttggtgc agagactgca      720
aattctttgc aggttcaagg ttctagtttg cctctgaatg tgaatggagc tagaacaaca     780
taccagcaat cgcaacagca acagccaatc atgcctaagc agcctggttt tggttatgga     840
acacaaatgg gtcagcttaa tagtcctggg ataagaggtg gtggtcttgt gggacttgga    900
gatcagtctt taacgaacaa tgtgggcttt gtccaaggtg cttctgctgc aattcctgga     960
gctttaggcg ttggtgctgt gtcgcctgtt acgccattgt catcagaagg gataggggaag   1020
agtaatggtg attcttcatc actctctccg tctccttaca tgttaatgg tggtgtgaga    1080
ggtagaaaga gtggcactgt ggagaaagtt gtagagagaa ggcaaaggag aatgataaag    1140
aaccgagaat cagctgcaag gtcccgggcc aggaaacagg cttacaccgt ggagcttgaa    1200
gctgaagttg caaagttaaa ggaagagaat gacgagttac aacgaaagca ggcaaggatc    1260
atggaaatgc aaaagaatca ggagacggag atgaggaatc ttctgcaagg aggtccaaag    1320
aaaaagctga ggaggacaga gtcgggacct tggtgaatca atcaatgcca tcatacttag    1380
tttctgtaga taaatgacat cccacttagg tgttttagtt gaattagact taatagagaa    1440
gagctttcat cgtttatatt gtaagctctc tccatatatg ttatgttttt tacatacaca    1500
ggatcatcag aatctctttt gctttattta gaccaagaat tttgtgtgtg tttctcgttg    1560
ttgttgtcg ttgtcgctat taaacctcaa aatgtacttt cttgatcttg gagttaccaa    1620
ttttgaagaa ttgaagtgtt gtttggttaa aaaa                                  1654
```

<210> SEQ ID NO: 4
<211> LENGTH: 416
<212> TYPE: PRT
<213> ORGANISM: Arabidopsis thaliana

<400> SEQUENCE: 4

```
Met Asp Gly Ser Met Asn Leu Gly Asn Glu Pro Pro Gly Asp Gly Gly
 1               5                  10                  15

Gly Gly Gly Gly Leu Thr Arg Gln Gly Ser Ile Tyr Ser Leu Thr Phe
            20                  25                  30

Asp Glu Phe Gln Ser Ser Val Gly Lys Asp Phe Gly Ser Met Asn Met
        35                  40                  45

Asp Glu Leu Leu Lys Asn Ile Trp Ser Ala Glu Glu Thr Gln Ala Met
    50                  55                  60

Ala Ser Gly Val Val Pro Val Leu Gly Gly Gln Glu Gly Leu Gln
65                  70                  75                  80

Leu Gln Arg Gln Gly Ser Leu Thr Leu Pro Arg Thr Leu Ser Gln Lys
```

```
            85                  90                  95
Thr Val Asp Gln Val Trp Lys Asp Leu Ser Lys Val Gly Ser Ser Gly
                100                 105                 110
Val Gly Gly Ser Asn Leu Ser Gln Val Ala Gln Ala Gln Ser Gln Ser
            115                 120                 125
Gln Ser Gln Arg Gln Gln Thr Leu Gly Glu Val Thr Leu Glu Glu Phe
    130                 135                 140
Leu Val Arg Ala Gly Val Val Arg Glu Glu Ala Gln Val Ala Ala Arg
145                 150                 155                 160
Ala Gln Ile Ala Glu Asn Asn Lys Gly Tyr Phe Gly Asn Asp Ala
                165                 170                 175
Asn Thr Gly Phe Ser Val Glu Phe Gln Gln Pro Ser Pro Arg Val Val
                180                 185                 190
Ala Ala Gly Val Met Gly Asn Leu Gly Ala Glu Thr Ala Asn Ser Leu
                195                 200                 205
Gln Val Gln Gly Ser Ser Leu Pro Leu Asn Val Asn Gly Ala Arg Thr
            210                 215                 220
Thr Tyr Gln Gln Ser Gln Gln Gln Pro Ile Met Pro Lys Gln Pro
225                 230                 235                 240
Gly Phe Gly Tyr Gly Thr Gln Met Gly Gln Leu Asn Ser Pro Gly Ile
                245                 250                 255
Arg Gly Gly Gly Leu Val Gly Leu Gly Asp Gln Ser Leu Thr Asn Asn
                260                 265                 270
Val Gly Phe Val Gln Gly Ala Ser Ala Ala Ile Pro Gly Ala Leu Gly
            275                 280                 285
Val Gly Ala Val Ser Pro Val Thr Pro Leu Ser Ser Glu Gly Ile Gly
            290                 295                 300
Lys Ser Asn Gly Asp Ser Ser Ser Leu Ser Pro Ser Pro Tyr Met Phe
305                 310                 315                 320
Asn Gly Gly Val Arg Gly Arg Lys Ser Gly Thr Val Glu Lys Val Val
                325                 330                 335
Glu Arg Arg Gln Arg Arg Met Ile Lys Asn Arg Glu Ser Ala Ala Arg
                340                 345                 350
Ser Arg Ala Arg Lys Gln Ala Tyr Thr Val Glu Leu Glu Ala Glu Val
            355                 360                 365
Ala Lys Leu Lys Glu Glu Asn Asp Glu Leu Gln Arg Lys Gln Ala Arg
    370                 375                 380
Ile Met Glu Met Gln Lys Asn Gln Glu Thr Glu Met Arg Asn Leu Leu
385                 390                 395                 400
Gln Gly Gly Pro Lys Lys Leu Arg Arg Thr Glu Ser Gly Pro Trp
                405                 410                 415

<210> SEQ ID NO: 5
<211> LENGTH: 1685
<212> TYPE: DNA
<213> ORGANISM: Arabidopsis thaliana

<400> SEQUENCE: 5
gaagcttgat cctcctagtt gtacgaaagc ttgagtaatg gggtctagat taaacttcaa      60
gagctttgtt gatggtgtga gtgagcagca gccaacggtg gggactagtc ttccattgac     120
taggcagaac tctgtgttct cgttaacctt tgatgagttt cagaactcat ggggtggtgg     180
aattgggaaa gattttgggt ctatgaacat ggatgagctc ttgaagaaca tttgactgc      240 agaggaaagt cattcaatga tgggaaacaa taccagttac accaacatca gcaatggtaa     300
```

```
tagtggaaac actgttatta acggcggtgg taacaacatt ggtgggttag ctgttggtgt    360
gggaggagaa agtggtggtt ttttcactgg tgggagtttg cagagacaag gttcacttac    420
cttgcctcgg acgattagtc agaaaagggt tgatgatgtc tggaaggagc tgatgaagga    480
ggatgacatt ggaaatggtg ttgttaatgg tgggacaagc ggaattccgc agaggcaaca    540
aacgctggga gagatgactt tggaggagtt tttggtcagg gctggtgtgg ttagggaaga    600
acctcaaccg gtggagagtg taactaactt caatggcgga ttctatggat ttggcagtaa    660
tggaggtctt gggacagcta gtaatgggtt tgttgcaaac caacctcaag atttgtcagg    720
aaatggagta gcggtgagac aggatctgct gactgctcaa actcagccac tacagatgca    780
gcagccacag atggtgcagc agccacagat ggtgcagcag ccgcaacaac tgatacagac    840
gcaggagagg cctttcccca acagaccac tatagcattt tccaacactg ttgatgtggt    900
taaccgttct caacctgcaa cacagtgcca ggaagtgaag ccttcaatac ttggaattca    960
taaccatcct atgaacaaca atctactgca agctgtcgat tttaaaacag gagtaacggt   1020
tgcagcagta tctcctggaa gccagatgtc acctgatctg actccaaaga gcgccctgga   1080
tgcatctttg tcccctgttc cttacatgtt tgggcgagtg agaaaaacag gtgcagttct   1140
ggagaaagtg attgagagaa ggcaaaaaag gatgataaag aatagggaat cagctgcaag   1200
atcccgcgct cgcaagcaag cttatacgat ggaactggaa gcagaaattg cgcaactcaa   1260
agaattgaat gaagagttgc agaagaaaca agttgaaatc atggaaaagc agaaaaatca   1320
gcttctggag cctctgcgcc agccatgggg aatgggatgc aaaaggcaat gcttgcgaag   1380
gacattgacg ggtccctggt agagcttata atggcgtcta aggaacccaa caaagcgccg   1440
aagttataga caaactcaga agatagaaag ctagctttgt acgtagttta ggcaggttct   1500
gtgggtgatt gtaaatcttg aagtgtggcg gatttgacag agatagataa acacatatct   1560
gttctatttt cctaaatctt ttggttttat cttcctgatg taatggatct ttatcatttg   1620
tcttgaacat ctttgtgact taaccagagt gaatttatct tgtatctaaa aaaaaaaaa    1680
aaaaa                                                                1685
```

<210> SEQ ID NO: 6
<211> LENGTH: 454
<212> TYPE: PRT
<213> ORGANISM: Arabidopsis thaliana

<400> SEQUENCE: 6

```
Met Gly Ser Arg Leu Asn Phe Lys Ser Phe Val Asp Gly Val Ser Glu
 1               5                  10                  15

Gln Gln Pro Thr Val Gly Thr Ser Leu Pro Leu Thr Arg Gln Asn Ser
            20                  25                  30

Val Phe Ser Leu Thr Phe Asp Glu Phe Gln Asn Ser Trp Gly Gly Gly
        35                  40                  45

Ile Gly Lys Asp Phe Gly Ser Met Asn Met Asp Glu Leu Leu Lys Asn
    50                  55                  60

Ile Trp Thr Ala Glu Glu Ser His Ser Met Met Gly Asn Asn Thr Ser
65                  70                  75                  80

Tyr Thr Asn Ile Ser Asn Gly Asn Ser Gly Asn Thr Val Ile Asn Gly
                85                  90                  95

Gly Gly Asn Asn Ile Gly Gly Leu Ala Val Gly Val Gly Glu Ser
            100                 105                 110

Gly Gly Phe Phe Thr Gly Gly Ser Leu Gln Arg Gln Gly Ser Leu Thr
```

-continued

```
            115                 120                 125
Leu Pro Arg Thr Ile Ser Gln Lys Arg Val Asp Asp Val Trp Lys Glu
    130                 135                 140
Leu Met Lys Glu Asp Asp Ile Gly Asn Gly Val Val Asn Gly Gly Thr
145                 150                 155                 160
Ser Gly Ile Pro Gln Arg Gln Gln Thr Leu Gly Glu Met Thr Leu Glu
                165                 170                 175
Glu Phe Leu Val Arg Ala Gly Val Val Arg Glu Glu Pro Gln Pro Val
                180                 185                 190
Glu Ser Val Thr Asn Phe Asn Gly Gly Phe Tyr Gly Phe Gly Ser Asn
            195                 200                 205
Gly Gly Leu Gly Thr Ala Ser Asn Gly Phe Val Ala Asn Gln Pro Gln
    210                 215                 220
Asp Leu Ser Gly Asn Gly Val Ala Val Arg Gln Asp Leu Leu Thr Ala
225                 230                 235                 240
Gln Thr Gln Pro Leu Gln Met Gln Pro Gln Met Val Gln Gln Pro
                245                 250                 255
Gln Met Val Gln Gln Pro Gln Gln Leu Ile Gln Thr Gln Glu Arg Pro
            260                 265                 270
Phe Pro Lys Gln Thr Thr Ile Ala Phe Ser Asn Thr Val Asp Val Val
    275                 280                 285
Asn Arg Ser Gln Pro Ala Thr Gln Cys Gln Glu Val Lys Pro Ser Ile
290                 295                 300
Leu Gly Ile His Asn His Pro Met Asn Asn Asn Leu Leu Gln Ala Val
305                 310                 315                 320
Asp Phe Lys Thr Gly Val Thr Val Ala Ala Val Ser Pro Gly Ser Gln
                325                 330                 335
Met Ser Pro Asp Leu Thr Pro Lys Ser Ala Leu Asp Ala Ser Leu Ser
            340                 345                 350
Pro Val Pro Tyr Met Phe Gly Arg Val Arg Lys Thr Gly Ala Val Leu
    355                 360                 365
Glu Lys Val Ile Glu Arg Arg Gln Lys Arg Met Ile Lys Asn Arg Glu
    370                 375                 380
Ser Ala Ala Arg Ser Arg Ala Arg Lys Gln Ala Tyr Thr Met Glu Leu
385                 390                 395                 400
Glu Ala Glu Ile Ala Gln Leu Lys Glu Leu Asn Glu Glu Leu Gln Lys
                405                 410                 415
Lys Gln Val Glu Ile Met Glu Lys Gln Lys Asn Gln Leu Leu Glu Pro
            420                 425                 430
Leu Arg Gln Pro Trp Gly Met Gly Cys Lys Arg Gln Cys Leu Arg Arg
    435                 440                 445
Thr Leu Thr Gly Pro Trp
    450
```

<210> SEQ ID NO: 7
<211> LENGTH: 1737
<212> TYPE: DNA
<213> ORGANISM: Arabidopsis thaliana

<400> SEQUENCE: 7

```
gaacaagggt tttagggctt ggatgctttg ttttcattga aaagaagta gaaggagtgt     60
atacaaggat tatgggaact cacatcaatt tcaacaactt aggaggtggt ggtcatcctg    120
gaggggaagg gagtagtaac cagatgaagc caacgggtag tgtcatgccc ttggctaggc    180
```

-continued

```
agtcctcggt ctactccctt acctttgatg agttacagaa cacactaggt ggaccgggaa    240
aagatttcgg gtcgatgaac atggatgaac tcctgaagag catatggact gctgaggaag    300
ctcaggccat ggccatgact tctgcgccag ctgctacagc ggtagcgcaa cctggtgctg    360
gtatcccacc cccaggtggg aatctccaga ggcaaggttc gttgacgttg cctagaacaa    420
ttagtcagaa gactgttgat gaggtgtgga aatgtttgat caccaaggat ggtaatatgg    480
aaggtagcag cggaggcggt ggtgagtcga atgtgcctcc tggaaggcaa cagactttag    540
gggaaatgac acttgaagaa tttctgttcc gtgctgggt tgtaagagaa gataactgtg     600
ttcaacagat gggtcaggtc aacggaaaca ataacaatgg gttttatggt aacagcactg    660
ctgctggcgg cttaggtttt ggatttggtc agccaaatca aaacagcata acattcaatg    720
gtactaatga ttctatgatc ttgaatcagc cacctggttt agggctcaaa atgggtggaa    780
caatgcagca gcaacaacaa caacagcagt tgcttcagca gcaacaacag cagatgcagc    840
agctgaatca gcctcatcca cagcagcggc tgcctcaaac cattttcct aaacaagcaa     900
acgtagcatt ttctgcgcct gtgaatataa ccaacaaggg ttttgctggg gctgcaaata    960
attctatcaa caataataat ggattagcta gttacggagg aaccgggtc actgttgcag     1020
caacttctcc aggaacaagc agcgcagaaa ataattcttt atcaccagtt ccgtatgtgc    1080
ttaatcgagg acgaagaagc aatacaggtc tagagaaggt tatcgagagg aggcaaagga    1140
gaatgatcaa gaatcgggaa tcagctgcta gatcaagagc tcgaaagcag gcttatacat    1200
tggaactgga agccgaaatt gaaaagctca agaaaacgaa tcaagaactg cagaaaaaac    1260
aggctgaaat ggtggaaatg cagaagaatg agctgaaaga aacgtcgaag cgaccgtggg    1320
gcagcaaaag gcaatgcttg agaaggacat taaccggacc atggtgaagg atgaagcaac    1380
aagaacggat gaaccagact cctagcttgg gattaatgta ataggatagt gctacctgta    1440
caggagatta agagaaattg agtgaaagat ctaggttaca gagtaggaga gagttttcat    1500
tatgaataaa tgacattttg tgccctgacc tttgttagtt taggtttaga ttatcctctg    1560
ttattgactt attgtgcttt ctggttgtta gggtttctaa aagacatagt tgtttatata    1620
tatgtctgac tttgtattcc ggatttggtt ctcttgtgtc attaacttgg gtttagccat    1680
tattacttaa gagtggcaac gaaatcaaaa aaaaaaaaa aaaaaaaaa aaaaaaa        1737
```

<210> SEQ ID NO: 8
<211> LENGTH: 431
<212> TYPE: PRT
<213> ORGANISM: Arabidopsis thaliana

<400> SEQUENCE: 8

```
Met Gly Thr His Ile Asn Phe Asn Asn Leu Gly Gly Gly His Pro
 1               5                  10                  15

Gly Gly Glu Gly Ser Ser Asn Gln Met Lys Pro Thr Gly Ser Val Met
             20                  25                  30

Pro Leu Ala Arg Gln Ser Ser Val Tyr Ser Leu Thr Phe Asp Glu Leu
         35                  40                  45

Gln Asn Thr Leu Gly Gly Pro Gly Lys Asp Phe Gly Ser Met Asn Met
     50                  55                  60

Asp Glu Leu Leu Lys Ser Ile Trp Thr Ala Glu Ala Gln Ala Met
 65                  70                  75                  80

Ala Met Thr Ser Ala Pro Ala Ala Thr Ala Val Ala Gln Pro Gly Ala
                 85                  90                  95

Gly Ile Pro Pro Pro Gly Gly Asn Leu Gln Arg Gln Gly Ser Leu Thr
```

-continued

```
                    100                 105                 110
Leu Pro Arg Thr Ile Ser Gln Lys Thr Val Asp Glu Val Trp Lys Cys
        115                 120                 125

Leu Ile Thr Lys Asp Gly Asn Met Glu Gly Ser Ser Gly Gly Gly
        130                 135                 140

Glu Ser Asn Val Pro Pro Gly Arg Gln Gln Thr Leu Gly Glu Met Thr
145                 150                 155                 160

Leu Glu Glu Phe Leu Phe Arg Ala Gly Val Val Arg Glu Asp Asn Cys
                165                 170                 175

Val Gln Gln Met Gly Gln Val Asn Gly Asn Asn Asn Gly Phe Tyr
                180                 185                 190

Gly Asn Ser Thr Ala Ala Gly Gly Leu Gly Phe Gly Phe Gly Gln Pro
        195                 200                 205

Asn Gln Asn Ser Ile Thr Phe Asn Gly Thr Asn Asp Ser Met Ile Leu
        210                 215                 220

Asn Gln Pro Pro Gly Leu Gly Leu Lys Met Gly Gly Thr Met Gln Gln
225                 230                 235                 240

Gln Gln Gln Gln Gln Leu Leu Gln Gln Gln Gln Gln Met Gln
                245                 250                 255

Gln Leu Asn Gln Pro His Pro Gln Gln Arg Leu Pro Gln Thr Ile Phe
                260                 265                 270

Pro Lys Gln Ala Asn Val Ala Phe Ser Ala Pro Val Asn Ile Thr Asn
        275                 280                 285

Lys Gly Phe Ala Gly Ala Ala Asn Ser Ile Asn Asn Asn Gly
        290                 295                 300

Leu Ala Ser Tyr Gly Gly Thr Gly Val Thr Val Ala Ala Thr Ser Pro
305                 310                 315                 320

Gly Thr Ser Ser Ala Glu Asn Asn Ser Leu Ser Pro Val Pro Tyr Val
                325                 330                 335

Leu Asn Arg Gly Arg Arg Ser Asn Thr Gly Leu Glu Lys Val Ile Glu
                340                 345                 350

Arg Arg Gln Arg Arg Met Ile Lys Asn Arg Glu Ser Ala Ala Arg Ser
        355                 360                 365

Arg Ala Arg Lys Gln Ala Tyr Thr Leu Glu Leu Glu Ala Glu Ile Glu
        370                 375                 380

Lys Leu Lys Lys Thr Asn Gln Glu Leu Gln Lys Lys Gln Ala Glu Met
385                 390                 395                 400

Val Glu Met Gln Lys Asn Glu Leu Lys Glu Thr Ser Lys Arg Pro Trp
                405                 410                 415

Gly Ser Lys Arg Gln Cys Leu Arg Arg Thr Leu Thr Gly Pro Trp
        420                 425                 430
```

<210> SEQ ID NO: 9
<211> LENGTH: 12
<212> TYPE: DNA
<213> ORGANISM: Arabidopsis thaliana

<400> SEQUENCE: 9
ggacacgtgg cg                                                    12

<210> SEQ ID NO: 10
<211> LENGTH: 36
<212> TYPE: DNA
<213> ORGANISM: Arabidopsis thaliana

<400> SEQUENCE: 10

```
ggacacgtgg cgggacacgt ggcgggacac gtggcg                                    36

<210> SEQ ID NO: 11
<211> LENGTH: 24
<212> TYPE: DNA
<213> ORGANISM: Arabidopsis thaliana

<400> SEQUENCE: 11
aattccggac acgtggcgta agct                                                 24

<210> SEQ ID NO: 12
<211> LENGTH: 24
<212> TYPE: DNA
<213> ORGANISM: Arabidopsis thaliana

<400> SEQUENCE: 12
aattccggac ctacagccta agct                                                 24

<210> SEQ ID NO: 13
<211> LENGTH: 24
<212> TYPE: DNA
<213> ORGANISM: Arabidopsis thaliana

<400> SEQUENCE: 13
aattccggac gcgtggccta agct                                                 24

<210> SEQ ID NO: 14
<211> LENGTH: 24
<212> TYPE: DNA
<213> ORGANISM: Arabidopsis thaliana

<400> SEQUENCE: 14
aattccggac ctacagccta agct                                                 24

<210> SEQ ID NO: 15
<211> LENGTH: 24
<212> TYPE: DNA
<213> ORGANISM: Arabidopsis thaliana

<400> SEQUENCE: 15
gaagcttgat cctcctagtt gtac                                                 24

<210> SEQ ID NO: 16
<211> LENGTH: 22
<212> TYPE: DNA
<213> ORGANISM: Arabidopsis thaliana

<400> SEQUENCE: 16
atttgaacaa gggttttagg gc                                                   22

<210> SEQ ID NO: 17
<211> LENGTH: 24
<212> TYPE: DNA
<213> ORGANISM: Arabidopsis thaliana

<400> SEQUENCE: 17
ttacaatcac ccacagaacc tgcc                                                 24

<210> SEQ ID NO: 18
<211> LENGTH: 21
<212> TYPE: DNA
<213> ORGANISM: Arabidopsis thaliana
```

-continued

```
<400> SEQUENCE: 18
gatttcgttg ccactcttaa g                                          21

<210> SEQ ID NO: 19
<211> LENGTH: 41
<212> TYPE: DNA
<213> ORGANISM: Arabidopsis thaliana
<220> FEATURE:
<221> NAME/KEY: misc_feature
<222> LOCATION: (1)...(41)
<223> OTHER INFORMATION: n = A,T,C or G

<400> SEQUENCE: 19
cagttgagcc gatcctgtcg nsgaggcgaa tcagtgcaac t                    41

<210> SEQ ID NO: 20
<211> LENGTH: 20
<212> TYPE: DNA
<213> ORGANISM: Arabidopsis thaliana

<400> SEQUENCE: 20
agttgcactg aattcgcctc                                            20

<210> SEQ ID NO: 21
<211> LENGTH: 20
<212> TYPE: DNA
<213> ORGANISM: Arabidopsis thaliana

<400> SEQUENCE: 21
cagttgagcg gatcctgtcg                                            20

<210> SEQ ID NO: 22
<211> LENGTH: 10
<212> TYPE: DNA
<213> ORGANISM: Arabidopsis thaliana

<400> SEQUENCE: 22
gacacgtgtc                                                       10

<210> SEQ ID NO: 23
<211> LENGTH: 10
<212> TYPE: DNA
<213> ORGANISM: Arabidopsis thaliana

<400> SEQUENCE: 23
gacacgtgtc                                                       10

<210> SEQ ID NO: 24
<211> LENGTH: 11
<212> TYPE: DNA
<213> ORGANISM: Arabidopsis thaliana
<220> FEATURE:
<221> NAME/KEY: misc_feature
<222> LOCATION: (1)...(11)
<223> OTHER INFORMATION: n = A,T,C or G

<400> SEQUENCE: 24
gntgacgtgg c                                                     11

<210> SEQ ID NO: 25
<211> LENGTH: 61
<212> TYPE: PRT
<213> ORGANISM: Arabidopsis thaliana

<400> SEQUENCE: 25
```

-continued

Pro Val Glu Lys Val Glu Arg Arg Gln Arg Met Ile Lys Asn
 1               5                  10                 15

Arg Glu Ser Ala Ala Arg Ser Arg Ala Arg Lys Gln Ala Tyr Thr Val
            20                  25                  30

Glu Leu Glu Ala Glu Leu Asn Met Leu Lys Glu Glu Asn Ala Gln Leu
        35                  40                  45

Lys Gln Ala Leu Ala Glu Ile Glu Arg Lys Arg Lys Gln
 50                  55                  60

<210> SEQ ID NO: 26
<211> LENGTH: 61
<212> TYPE: PRT
<213> ORGANISM: Arabidopsis thaliana

<400> SEQUENCE: 26

Pro Met Glu Lys Thr Val Glu Arg Arg Gln Lys Arg Met Ile Lys Asn
 1               5                  10                 15

Arg Glu Ser Ala Ala Arg Ser Arg Ala Arg Lys Gln Ala Tyr Thr His
            20                  25                  30

Glu Leu Glu Asn Lys Val Ser Arg Leu Glu Glu Asn Glu Arg Leu
        35                  40                  45

Arg Arg Glu Lys Glu Val Glu Lys Val Ile Pro Trp Val
 50                  55                  60

<210> SEQ ID NO: 27
<211> LENGTH: 61
<212> TYPE: PRT
<213> ORGANISM: Arabidopsis thaliana

<400> SEQUENCE: 27

Pro Ile Glu Lys Thr Val Glu Arg Arg Gln Lys Arg Met Ile Lys Asn
 1               5                  10                 15

Arg Glu Ser Ala Ala Arg Ser Arg Ala Arg Lys Gln Ala Tyr Thr His
            20                  25                  30

Glu Leu Glu Asn Lys Ile Ser Arg Leu Glu Glu Glu Asn Glu Leu Leu
        35                  40                  45

Lys Arg Gln Lys Glu Val Gly Met Val Leu Pro Ser Ala
 50                  55                  60

<210> SEQ ID NO: 28
<211> LENGTH: 61
<212> TYPE: PRT
<213> ORGANISM: Arabidopsis thaliana

<400> SEQUENCE: 28

Pro Asn Asp Thr Thr Asp Glu Arg Lys Arg Lys Arg Met Leu Ser Asn
 1               5                  10                 15

Arg Glu Ser Ala Arg Arg Ser Arg Ala Arg Lys Gln Gln Arg Leu Glu
            20                  25                  30

Glu Leu Val Ala Glu Val Ala Arg Leu Gln Ala Glu Asn Ala Ala Thr
        35                  40                  45

Gln Ala Arg Thr Ala Ala Leu Glu Arg Asp Leu Gly Arg
 50                  55                  60

<210> SEQ ID NO: 29
<211> LENGTH: 61
<212> TYPE: PRT
<213> ORGANISM: Arabidopsis thaliana

```
<400> SEQUENCE: 29

Pro Met Asp Glu Arg Glu Leu Lys Arg Glu Arg Lys Gln Ser Asn
1               5                   10                  15

Arg Glu Ser Ala Arg Arg Ser Arg Leu Arg Lys Gln Gln Glu Cys Glu
            20                  25                  30

Glu Leu Ala Gln Lys Val Ser Glu Leu Thr Ala Ala Asn Gly Thr Leu
        35                  40                  45

Arg Ser Glu Leu Asp Gln Leu Lys Lys Asp Cys Lys Thr
    50                  55                  60

<210> SEQ ID NO: 30
<211> LENGTH: 61
<212> TYPE: PRT
<213> ORGANISM: Arabidopsis thaliana

<400> SEQUENCE: 30

Pro Lys Asp Asp Lys Glu Ser Lys Arg Glu Arg Lys Gln Ser Asn
1               5                   10                  15

Arg Glu Ser Ala Arg Arg Ser Arg Leu Arg Lys Gln Ala Glu Thr Glu
            20                  25                  30

Glu Leu Ala Arg Lys Val Glu Leu Leu Thr Ala Glu Asn Thr Ser Leu
        35                  40                  45

Arg Arg Glu Ile Ser Arg Leu Thr Glu Ser Ser Lys Lys
    50                  55                  60

<210> SEQ ID NO: 31
<211> LENGTH: 61
<212> TYPE: PRT
<213> ORGANISM: Arabidopsis thaliana

<400> SEQUENCE: 31

Pro Gln Asn Glu Arg Glu Leu Lys Arg Glu Arg Lys Gln Ser Asn
1               5                   10                  15

Arg Glu Ser Ala Arg Arg Ser Arg Leu Arg Lys Gln Ala Glu Thr Glu
            20                  25                  30

Glu Leu Ala Arg Lys Val Glu Ala Leu Thr Ala Glu Asn Met Ala Leu
        35                  40                  45

Arg Ser Glu Leu Asn Gln Leu Asn Glu Lys Ser Asp Lys
    50                  55                  60

<210> SEQ ID NO: 32
<211> LENGTH: 61
<212> TYPE: PRT
<213> ORGANISM: Arabidopsis thaliana

<400> SEQUENCE: 32

Pro Gln Asn Glu Arg Glu Leu Lys Arg Glu Lys Arg Lys Gln Ser Asn
1               5                   10                  15

Arg Glu Ser Ala Arg Arg Ser Arg Leu Arg Lys Gln Ala Glu Ala Glu
            20                  25                  30

Glu Leu Ala Ile Arg Val Gln Ser Leu Thr Ala Glu Asn Met Thr Leu
        35                  40                  45

Lys Ser Glu Ile Asn Lys Leu Met Glu Asn Ser Glu Lys
    50                  55                  60

<210> SEQ ID NO: 33
<211> LENGTH: 40
<212> TYPE: DNA
<213> ORGANISM: Arabidopsis thaliana
```

```
<400> SEQUENCE: 33
ggatcctgtc gtggggacac gtggcatacg aggcgaattc                              40

<210> SEQ ID NO: 34
<211> LENGTH: 40
<212> TYPE: DNA
<213> ORGANISM: Arabidopsis thaliana

<400> SEQUENCE: 34
ggatcctgtc ggggacacgt ggcgctaacg aggcgaattc                              40

<210> SEQ ID NO: 35
<211> LENGTH: 40
<212> TYPE: DNA
<213> ORGANISM: Arabidopsis thaliana

<400> SEQUENCE: 35
ggatcctgtc gggacacgtg gcgcaacacg aggcgaattc                              40

<210> SEQ ID NO: 36
<211> LENGTH: 40
<212> TYPE: DNA
<213> ORGANISM: Arabidopsis thaliana

<400> SEQUENCE: 36
ggatcctgtc gggacacgtg gcccacccgg aggcgaattc                              40

<210> SEQ ID NO: 37
<211> LENGTH: 40
<212> TYPE: DNA
<213> ORGANISM: Arabidopsis thaliana

<400> SEQUENCE: 37
ggatcctgtc gggacacgtg gcacaaatag aggcgaattc                              40

<210> SEQ ID NO: 38
<211> LENGTH: 40
<212> TYPE: DNA
<213> ORGANISM: Arabidopsis thaliana

<400> SEQUENCE: 38
ggatcctgtc gtcaatggac acgtggctag aggcgaattc                              40

<210> SEQ ID NO: 39
<211> LENGTH: 40
<212> TYPE: DNA
<213> ORGANISM: Arabidopsis thaliana

<400> SEQUENCE: 39
ggatcctgtc gtcggacacg tggcacgaag aggcgaattc                              40

<210> SEQ ID NO: 40
<211> LENGTH: 40
<212> TYPE: DNA
<213> ORGANISM: Arabidopsis thaliana

<400> SEQUENCE: 40
gaattcgcct cgacaggaca cgtggcacgc gacaggatcc                              40

<210> SEQ ID NO: 41
<211> LENGTH: 40
<212> TYPE: DNA
```

<213> ORGANISM: Arabidopsis thaliana

<400> SEQUENCE: 41
ggatcctgtc gatcaatgga cacgtggcag aggcgaattc          40

<210> SEQ ID NO: 42
<211> LENGTH: 40
<212> TYPE: DNA
<213> ORGANISM: Arabidopsis thaliana

<400> SEQUENCE: 42
gaattcgcct cggtgacacg tggcttgacc gacaggatcc          40

<210> SEQ ID NO: 43
<211> LENGTH: 40
<212> TYPE: DNA
<213> ORGANISM: Arabidopsis thaliana

<400> SEQUENCE: 43
ggatcctgtc ggaagtggtg acacgtggcg aggcgaattc          40

<210> SEQ ID NO: 44
<211> LENGTH: 40
<212> TYPE: DNA
<213> ORGANISM: Arabidopsis thaliana

<400> SEQUENCE: 44
gaattcgcct caagaggtga cacgtggcac gacaggatcc          40

<210> SEQ ID NO: 45
<211> LENGTH: 40
<212> TYPE: DNA
<213> ORGANISM: Arabidopsis thaliana

<400> SEQUENCE: 45
ggatcctgtc gcgacacgtg gctgttagtg aggcgaattc          40

<210> SEQ ID NO: 46
<211> LENGTH: 40
<212> TYPE: DNA
<213> ORGANISM: Arabidopsis thaliana

<400> SEQUENCE: 46
gaattcgcct ctaaggaaca cgtggcccgc gacaggatcc          40

<210> SEQ ID NO: 47
<211> LENGTH: 40
<212> TYPE: DNA
<213> ORGANISM: Arabidopsis thaliana

<400> SEQUENCE: 47
gaattcgcct ccgggcggaa cacgtggcac gacaggatcc          40

<210> SEQ ID NO: 48
<211> LENGTH: 40
<212> TYPE: DNA
<213> ORGANISM: Arabidopsis thaliana

<400> SEQUENCE: 48
ggatcctgtc gcgtgggtac acgtggcccg aggcgaattc          40

<210> SEQ ID NO: 49
<211> LENGTH: 40

-continued

```
<212> TYPE: DNA
<213> ORGANISM: Arabidopsis thaliana

<400> SEQUENCE: 49
ggatcctgtc gcggtcttta tgacacgtgg aggcgaattc          40

<210> SEQ ID NO: 50
<211> LENGTH: 40
<212> TYPE: DNA
<213> ORGANISM: Arabidopsis thaliana

<400> SEQUENCE: 50
gaattcgcct cggacacgtg tsgcgatccc gacaggatcc          40

<210> SEQ ID NO: 51
<211> LENGTH: 40
<212> TYPE: DNA
<213> ORGANISM: Arabidopsis thaliana

<400> SEQUENCE: 51
gaattcgcct ctaaggcggg acacgtgtsc gacaggatcc          40

<210> SEQ ID NO: 52
<211> LENGTH: 39
<212> TYPE: DNA
<213> ORGANISM: Arabidopsis thaliana

<400> SEQUENCE: 52
gaattcgcct ctgacactgt cagtcccacg acaggatcc           39

<210> SEQ ID NO: 53
<211> LENGTH: 40
<212> TYPE: DNA
<213> ORGANISM: Arabidopsis thaliana

<400> SEQUENCE: 53
gaattcgcct cggggccacg tggcttccgc gacaggatcc          40

<210> SEQ ID NO: 54
<211> LENGTH: 40
<212> TYPE: DNA
<213> ORGANISM: Arabidopsis thaliana

<400> SEQUENCE: 54
gaattcgcct cttcgatggc cacgtggcgc gacaggatcc          40

<210> SEQ ID NO: 55
<211> LENGTH: 40
<212> TYPE: DNA
<213> ORGANISM: Arabidopsis thaliana

<400> SEQUENCE: 55
gaattcgcct cttaagtggc cacgtggcgc gacaggatcc          40

<210> SEQ ID NO: 56
<211> LENGTH: 40
<212> TYPE: DNA
<213> ORGANISM: Arabidopsis thaliana

<400> SEQUENCE: 56
gaattcgcct ctcacgaggc cacgtggcac gacaggatcc          40

<210> SEQ ID NO: 57
```

```
<211> LENGTH: 40
<212> TYPE: DNA
<213> ORGANISM: Arabidopsis thaliana

<400> SEQUENCE: 57
gaattcgcct ccgtggcgcc acgtggccgc gacaggatcc                40

<210> SEQ ID NO: 58
<211> LENGTH: 40
<212> TYPE: DNA
<213> ORGANISM: Arabidopsis thaliana

<400> SEQUENCE: 58
gaattcgcct caatgcaccg ccacgtggcc gacaggatcc                40

<210> SEQ ID NO: 59
<211> LENGTH: 40
<212> TYPE: DNA
<213> ORGANISM: Arabidopsis thaliana

<400> SEQUENCE: 59
gaattcgcct ccctgactgc cacgtggcac gacaggatcc                40

<210> SEQ ID NO: 60
<211> LENGTH: 40
<212> TYPE: DNA
<213> ORGANISM: Arabidopsis thaliana

<400> SEQUENCE: 60
gaattcgcct ccaagcgttc gccacgtggc gacaggatcc                40

<210> SEQ ID NO: 61
<211> LENGTH: 40
<212> TYPE: DNA
<213> ORGANISM: Arabidopsis thaliana

<400> SEQUENCE: 61
gaattcgcct ctttgtccac gtggcccacc gacaggatcc                40

<210> SEQ ID NO: 62
<211> LENGTH: 40
<212> TYPE: DNA
<213> ORGANISM: Arabidopsis thaliana

<400> SEQUENCE: 62
gaattcgcct ctagaccgtc cacgtggccc gacaggatcc                40

<210> SEQ ID NO: 63
<211> LENGTH: 40
<212> TYPE: DNA
<213> ORGANISM: Arabidopsis thaliana

<400> SEQUENCE: 63
gaattcgcct ctaccacgtg gcacaccgtc gacaggatcc                40

<210> SEQ ID NO: 64
<211> LENGTH: 40
<212> TYPE: DNA
<213> ORGANISM: Arabidopsis thaliana

<400> SEQUENCE: 64
ggatcctgtc ggctaccacg tggcaagaag aggcgaattc                40
```

-continued

<210> SEQ ID NO: 65
<211> LENGTH: 40
<212> TYPE: DNA
<213> ORGANISM: Arabidopsis thaliana

<400> SEQUENCE: 65
gaattcgcct cccttagcac cacgtggcac gacaggatcc                    40

<210> SEQ ID NO: 66
<211> LENGTH: 40
<212> TYPE: DNA
<213> ORGANISM: Arabidopsis thaliana

<400> SEQUENCE: 66
ggatcctgtc ggttcgatga cgtggcgagg aggcgaattc                    40

<210> SEQ ID NO: 67
<211> LENGTH: 40
<212> TYPE: DNA
<213> ORGANISM: Arabidopsis thaliana

<400> SEQUENCE: 67
ggatcctgtc ggcttgatga cgtggccacg aggcgaattc                    40

<210> SEQ ID NO: 68
<211> LENGTH: 40
<212> TYPE: DNA
<213> ORGANISM: Arabidopsis thaliana

<400> SEQUENCE: 68
gaattcgcct ccttgatgac gtggcaccac gacaggatcc                    40

<210> SEQ ID NO: 69
<211> LENGTH: 40
<212> TYPE: DNA
<213> ORGANISM: Arabidopsis thaliana

<400> SEQUENCE: 69
ggatcctgtc gtggctgacg tggcactagg aggcgaattc                    40

<210> SEQ ID NO: 70
<211> LENGTH: 40
<212> TYPE: DNA
<213> ORGANISM: Arabidopsis thaliana

<400> SEQUENCE: 70
ggatcctgtc ggcgcgtggt gacgtggccg aggcgaattc                    40

<210> SEQ ID NO: 71
<211> LENGTH: 40
<212> TYPE: DNA
<213> ORGANISM: Arabidopsis thaliana

<400> SEQUENCE: 71
ggattctgtc gattcggtga cgtgtcccgg aggcgaattc                    40

<210> SEQ ID NO: 72
<211> LENGTH: 40
<212> TYPE: DNA
<213> ORGANISM: Arabidopsis thaliana

<400> SEQUENCE: 72
gaattcgcct ctggctgctg acgtgtcccc gacaggatcc                    40

-continued

<210> SEQ ID NO: 73
<211> LENGTH: 40
<212> TYPE: DNA
<213> ORGANISM: Arabidopsis thaliana

<400> SEQUENCE: 73
ggatcctgtc gacgtggcaa cttgaacgcg aggcgaattc          40

<210> SEQ ID NO: 74
<211> LENGTH: 40
<212> TYPE: DNA
<213> ORGANISM: Arabidopsis thaliana

<400> SEQUENCE: 74
gaattcgcct cgccctgaag tggacagcgc gacaggatcc          40

<210> SEQ ID NO: 75
<211> LENGTH: 40
<212> TYPE: DNA
<213> ORGANISM: Arabidopsis thaliana

<400> SEQUENCE: 75
gaattcgcct cgccctgaag tggacagcgc gacaggatcc          40

<210> SEQ ID NO: 76
<211> LENGTH: 40
<212> TYPE: DNA
<213> ORGANISM: Arabidopsis thaliana

<400> SEQUENCE: 76
gaattcgcct cccgtccgcg tggcagcagc gacaggatcc          40

<210> SEQ ID NO: 77
<211> LENGTH: 40
<212> TYPE: DNA
<213> ORGANISM: Arabidopsis thaliana

<400> SEQUENCE: 77
ggatcctgtc ggcgcgtggt gacgtggccg aggcgaattc          40

<210> SEQ ID NO: 78
<211> LENGTH: 40
<212> TYPE: DNA
<213> ORGANISM: Arabidopsis thaliana

<400> SEQUENCE: 78
ggatcctgtc gcgtgggtac acgtggcccg aggcgaattc          40

<210> SEQ ID NO: 79
<211> LENGTH: 40
<212> TYPE: DNA
<213> ORGANISM: Arabidopsis thaliana

<400> SEQUENCE: 79
ggatcctgtc gcgtgccacg tgtcctgtcg aggcgaattc          40

<210> SEQ ID NO: 80
<211> LENGTH: 60
<212> TYPE: PRT
<213> ORGANISM: Arabidopsis thaliana

<400> SEQUENCE: 80

Leu Glu Lys Val Val Glu Arg Arg Gln Lys Arg Met Ile Lys Asn Arg

-continued

```
                1               5                  10                    15
Glu Ser Ala Ala Arg Ser Arg Ala Arg Lys Gln Ala Tyr Thr Leu Glu
                    20                  25                  30

Leu Glu Ala Glu Ile Glu Ser Leu Lys Leu Val Asn Gln Asp Leu Gln
            35                  40                  45

Lys Lys Gln Ala Glu Ile Met Lys Thr His Asn Ser
        50                  55                  60
```

<210> SEQ ID NO: 81
<211> LENGTH: 60
<212> TYPE: PRT
<213> ORGANISM: Arabidopsis thaliana

<400> SEQUENCE: 81

```
Val Glu Lys Val Val Glu Arg Arg Gln Arg Arg Met Ile Lys Asn Arg
 1               5                  10                  15

Glu Ser Ala Ala Arg Ser Arg Ala Arg Lys Gln Ala Tyr Thr Val Glu
                    20                  25                  30

Leu Glu Ala Glu Val Ala Lys Leu Lys Glu Glu Asn Asp Glu Leu Gln
            35                  40                  45

Arg Lys Gln Ala Arg Ile Met Glu Met Gln Lys Asn
        50                  55                  60
```

<210> SEQ ID NO: 82
<211> LENGTH: 60
<212> TYPE: PRT
<213> ORGANISM: Arabidopsis thaliana

<400> SEQUENCE: 82

```
Leu Glu Lys Val Ile Glu Arg Arg Gln Lys Arg Met Ile Lys Arg Arg
 1               5                  10                  15

Glu Ser Ala Ala Arg Ser Arg Ala Arg Lys Gln Ala Tyr Thr Met Glu
                    20                  25                  30

Leu Glu Ala Glu Ile Ala Gln Leu Lys Glu Leu Asn Glu Glu Leu Gln
            35                  40                  45

Lys Lys Gln Val Glu Ile Met Glu Lys Gln Lys Asn
        50                  55                  60
```

<210> SEQ ID NO: 83
<211> LENGTH: 60
<212> TYPE: PRT
<213> ORGANISM: Arabidopsis thaliana

<400> SEQUENCE: 83

```
Leu Glu Lys Val Ile Glu Arg Arg Gln Arg Arg Met Ile Lys Asn Arg
 1               5                  10                  15

Glu Ser Ala Ala Arg Ser Arg Ala Arg Lys Gln Ala Tyr Thr Leu Glu
                    20                  25                  30

Leu Glu Ala Glu Ile Glu Lys Leu Lys Lys Thr Asn Gln Glu Leu Gln
            35                  40                  45

Lys Lys Gln Ala Glu Met Val Glu Met Gln Lys Asn
        50                  55                  60
```